(12) United States Patent
Samuel et al.

(10) Patent No.: US 8,536,333 B2
(45) Date of Patent: *Sep. 17, 2013

(54) NEUTRAL METALLIC DENDRIMER COMPLEXES

(75) Inventors: Ifor David William Samuel, Fife (GB);
Paul Leslie Burn, Oxford (GB);
Shih-Chun Lo, Oxford (GB)

(73) Assignees: Isis Innovation Limited, Oxford (GB);
The University Court of the University of St. Andrews, Fife (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/854,288

(22) Filed: Aug. 11, 2010

(65) Prior Publication Data

US 2011/0127496 A1 Jun. 2, 2011

Related U.S. Application Data

(63) Continuation of application No. 10/525,687, filed as application No. PCT/GB03/03725 on Aug. 28, 2003, now Pat. No. 7,799,917.

(30) Foreign Application Priority Data

Aug. 28, 2002 (GB) .................................. 0219987.5

(51) Int. Cl.
*C07F 15/00* (2006.01)
*H01L 51/50* (2006.01)

(52) U.S. Cl.
USPC ................................ 546/2; 313/504; 428/690

(58) Field of Classification Search
USPC .............................. 546/2; 428/690; 313/504
See application file for complete search history.

(56) References Cited

U.S. PATENT DOCUMENTS 7,592,074 B2 9/2009 Burn et al.
7,799,917 B2 9/2010 Samuel et al.

FOREIGN PATENT DOCUMENTS

| JP | 2003231692 A | 8/2003 |
|---|---|---|
| WO | W00214376 A2 | 2/2002 |
| WO | WO02066552 A1 | 8/2002 |
| WO | WO02081488 A1 | 10/2002 |
| WO | WO03079736 A1 | 9/2003 |

OTHER PUBLICATIONS

Adronov, et al., Light-Harvesting Dendrimers, Chem. Commun., 2000, pp. 1701-1710.
Balzani, et al., Dendrimers Based on Photoactive Metal Complexes. Recent Advances, Coord. Chem. Rev., 2001, 291-221, pp. 545-572.
Freeman, et al., Dendrimer-Containing Light-Emitting Diodes: Toward Site-Isolation of Chromophores, J. Am. Chem. Soc., 2000, vol. 122, No. 49, pp. 12385-12386.
Gong, et al., Trifunctional Light-Emitting Molecules Based on Rhenium and Ruthenium Bipyridine Complexes, Adv. Mater., 1998, vol. 10, No. 16, pp. 1337-1340.
Halim, et al., Conjugated Dendrimers for Light-Emitting Diodes: Effect of Generation, Adv. Mater., 1999, vol. 11, No. 5, pp. 371-374.
Kimura, et al., Energy Transfer Within Ruthenium-Cored Rigid Metallodendrimers, Tetrahedron Letters, 2000, vol. 41, pp. 6809-6813.
Kwok, et al., Synthesis and Light-Emitting Properties of Difunctional Dendritic Distyrylstilbenes, Macromolecules, 2001, vol. 34, pp. 6821-6830.
Lo, et al., Green Phosphorescent Dendrimer for Light-Emitting Diodes, Adv. Mater., 2002, vol. 14, No. 13-14, pp. 975-979.
Lupton, et al., Control of Electrophosphorescence in Conjugated Dendrimer Light-Emitting Diodes, Adv. Funct. Mater., 2001, vol. 11, No. 4, August, pp. 287-294.
Lupton, et al., Control of Mobility in Molecular Organic Semiconductors by Dendrimer Generation, Phys. Rev. B, 2001, vol. 63, pp. 155206-1 thru 155206-8.
Markham, et al., High-Efficiency Green Phosphorescence from Spin-Coated Single-Layer Dendrimer Light-Emitting Diodes, Appl. Phys. Lett., 2002, vol. 80, No. 15, pp. 2645-2647.
Wang, et al., Electroluminescent Diodes from a Single-Component Emitting Layer of Dendritic Macromolecules, Adv. Mater., 1996, vol. 8, No. 3, pp. 237-241.
Xie, et al., Reduction of Self-Quenching Effect in Organic Electrophosphorescence Emitting Devices Via the Use of Sterically Hindered Spacers in Phosphorescence Molecules, Adv. Mater., 2001, vol. 13, No. 16, pp. 1245-1248.
PCT International Search Report, PCT/GB03/03725, Jan. 20, 2004.
The Patent Office, Search Report, No. GB 0219987.5, Jan. 23, 2003.
United States Patent and Trademark Office, Office Action Summary and Detailed Action, U.S. Appl. No. 10/525,687, Aug. 28, 2008.
United States Patent and Trademark Office, Office Action Summary and Detailed Action, U.S. Appl. No. 10/525,687, Apr. 10, 2009.
United States Patent and Trademark Office, Office Action Summary and Detailed Action, U.S. Appl. No. 10/525,687, Dec. 2, 2009.

*Primary Examiner* — Charanjit Aulakh
(74) *Attorney, Agent, or Firm* — Quarles & Brady LLP

(57) ABSTRACT

A charge-neutral organometallic dendrimer is described, said dendrimer having the formula (I):

CORE-[DENDRITE(-Q)$_a$]$_n$   (I)

in which CORE represents a group of formula $MX_xY_z$, in which M represents a metal cation, x represents an integer of 1 or more, each X which may be the same or different represents a mono-, bi- or tri-dentate coordinating group, z represents 0 or an integer of 1 or more, and each Y which may be the same or different represents a coordinating group, the total of (b.x)+(c.z) being equal to the number of coordination sites on M, wherein b is the number of coordination sites on X and c is the number of coordination sites on Y; n represents an integer of 2 or more; each DENDRITE which may be the same or different represents a dendritic molecular structure bonded to a group X; a represents 0 or an integer of 1 or more; and each Q which may be the same or different represents a surface group; CORE terminating in the first single bond which is connected to a branching group or branching atom of DENDRITE; which dendrimer has a structure in which no hemisphere of a notional sphere centered on M and containing the dendrimer is devoid of a said first single bond.

29 Claims, 11 Drawing Sheets

Dendrimer A of generation 2          Dendrimer B of generation 3

Octahedral

A
Comparative example

B
Current invention

Square planar cis
X
Comparative example trans
Y
Current invention

NEUTRAL METALLIC DENDRIMER COMPLEXES

CROSS-REFERENCE TO RELATED APPLICATIONS

This is a continuation application of U.S. application Ser. No. 10/525,687 filed Jul. 26, 2005 now U.S. Pat. No. 7,799,917, which is a 371 of PCT/GB03/03725 filed Aug. 28, 2003.

This invention relates to dendrimers, a process for forming them, and their use in electro-optic devices, in particular light-emitting devices.

BACKGROUND

Organic light-emitting diodes (OLEDs), also known as organic electroluminescent (EL) devices, are an emerging display technology. In essence an OLED comprises a thin organic layer or stack of organic layers sandwiched between two electrodes, such that when a voltage is applied visible or other light is emitted. At least one of the electrodes must be transparent to light. For display applications the light must of course be visible to the eye, and therefore at least one of the electrodes must be transparent to visible light.

There are two principal techniques that can be used to deposit the organic layers in an OLED: thermal evaporation and solution processing. Solution processing has the potential to be the lower cost technique due to its potentially greater throughput and ability to handle large substrate sizes. Significant work has been undertaken to develop appropriate materials, particularly polymers. More recently phosphorescent organometallic dendrimers that are luminescent in the solid state have been shown to have great promise as solution processible light-emitting materials in OLEDs (S.-C. Lo, et al *Adv. Mater.*, 2002, 13, 975; J. P. J. Markham, et al *Appl. Phys. Lett.*, 2002,80,2645). Although progress has been made in the development of solution processible OLEDs there is still the need for OLEDs with improved efficiency and lifetime.

Dendrimers are branched macromolecules with a core and attached dendrons (also called dendrites). Dendrons are branched structures comprising branching units and optionally linking units. The generation of a dendron is defined by the number of sets of branching points; see FIG. 1. Dendrons of a higher generation, or order, can be composed of the same structural units (branching and linking units) but have an additional level of branching, i.e. an additional repetition of these branching and linking units. Alternatively higher generations can have an additional level of branching but different branching and linking units at the higher generation. There can be surface groups on the periphery of the dendrons.

Light-emitting dendrimers typically have a luminescent core and in many cases at least partially conjugated dendrons. Further examples of light-emitting dendrimers include those found in P. W. Wang, et al *Adv. Mater.*, 1996, 8, 237; M. Halim, et al *Adv. Mater.*, 1999, 11, 371; A. W. Freeman, et al *J. Am. Chem. Soc.*, 2000, 122, 12385; A. Adronov, et al *Chem. Comm.* 2000, 1701.; C. C. Kwok, et al *Macromolecules*, 2001, 34, 6821. Light-emitting dendrimers have the advantage over light-emitting polymers that the light-emitting properties and the processing properties can be independently optimised as the nature of the core, dendrons and surface groups can be independently altered. For example, the emission colour of a dendrimer can be changed by simply changing the core. Such light-emitting dendrimers can be useful in electro-optic devices, particularly OLEDs.

Other physical properties, such as viscosity, may also make dendrimers more easily tailored to the available manufacturing processes than polymers. Organometallic dendrimers have previously been used in OLED applications as a single component in a film (i.e. a neat film) or in a blend with a molecular material or in a blend of more than one dendrimer of different type (i.e. different cores), e.g. J. M. Lupton et al. *Adv. Funct. Mater.*, 2001, 11, 287 and J. P. J. Markham, et al *Appl. Phys. Lett.*, 2002, 80, 2645.

Intermolecular interactions play an important role in the opto-electronic properties of organic light-emitting and transport materials. Close contact and good order can lead to high charge mobilities but can also give rise to reduced emission due to the formation of excited state dimers. In previous work we have shown that intermolecular interactions can be controlled by the generation of the dendrons attached to a dendrimer (J. M. Lupton, et al *Phys. Rev. B*, 2001, 63, 5206; J. P. J. Markham, et al *Appl. Phys. Lett.*, 2002, 80, 2645). However, we have found that for organometallic dendrimers that contain only one dendron per ligand that generation does not always give adequate control over intermolecular interactions. For example, for the iridium based dendrimers in J. P. J. Markham, et al *Appl. Phys. Lett.*, 2002, 80, 2645 (see FIG. 2), the photoluminescence quantum yield of the second generation, 2, is higher than for the first, 1, but both are less than when the measurement is carried out in dilute solution where dendrimer intermolecular interactions are not present. For iridium dendrimers 1 and 2 the dendrons are attached to one component of the bidentate ligand, namely the phenyl ring, and the facial (fac) isomers are formed. This combination leaves one face of the core unprotected by dendrons allowing potentially detrimental core-core interactions.

There are known dendrimers based on tris ruthenium 2,2'-bipyridine cores in V. Balzani, et al *Coord. Chem. Rev.* 2001, 291-221, 545. In these dendrimers two dendrons are attached to each 2,2'-bipyridine ligand at the 4 and 4' positions. However 2,2'-bipyridine is a neutral ligand, and these dendritic complexes have a net positive charge which has to be balanced by an associated counter-ion, typically $PF_6^-$. The three bipyridine ligands fill the coordination sphere of Ru, so the counter-ion is not part of the inner coordination sphere of the metal, but is more loosely associated. In OLED applications it is undesirable to have unbound counter-ions, as these may be able to migrate under the influence of the applied field, which could be detrimental to the OLED device stability. The present invention relates to organometallic dendrimers that are neutral, i.e. those in which the ligands directly coordinated/bonded to the metal balance the charge.

We have discovered that these disadvantageous core-core interactions that are detrimental to OLEDs can be overcome by changing the dendrimer structure. One way of doing this is to attach more than one dendron to more than one ligand complexed to the metal cation. For example, for an octahedral fac-iridium (III) complex with 2-phenylpyridine ligands a dendron could be attached to both the phenyl and pyridyl rings and then two or more of these ligands complexed to the metal cation. In this embodiment of the invention, the organometallic dendrimers contain more than one dendron attached to each ligand.

A second way of controlling the intermolecular core-core interactions is by using different isomers. For example, for an octahedral fac-iridium (III) complex with 2-phenylpyridine ligands with dendrons attached to the phenyl rings one face of the core is not protected by the dendron. By using the meridinal (mer) isomer the dendrons are more evenly distributed around the core and as a consequence the core is more protected by the dendrons.

The present invention relates to dendrimers, processes of preparing them and opto-electronic devices, in particular OLEDs, containing them, that solve some of the problems in the prior art. In particular, the invention seeks to overcome the intermolecular interactions that are detrimental for OLED performance.

SUMMARY OF THE INVENTION

The present invention accordingly provides a charge-neutral organometallic dendrimer of formula (I):

$$\text{CORE-[DENDRITE(-Q)}_a]_n \qquad (I)$$

in which CORE represents a group of formula $MX_xY_z$, in which M represents a metal cation, x represents an integer of 1 or more, each X which may be the same or different represents a mono-, bi- or tri-dentate coordinating group, z represents 0 or an integer of 1 or more, and each Y which may be the same or different represents a coordinating group, the total of (b.x)+(c.z) being equal to the number of coordination sites on M, wherein b is the number of coordination sites on X and c is the number of coordination sites on Y; n represents an integer of 2 or more; each DENDRITE which may be the same or different represents a dendritic molecular structure bonded to a group X; a represents 0 or an integer of 1 or more; and each Q which may be the same or different represents a surface group; CORE terminating in the first single bond which is connected to a branching group or branching atom of DENDRITE; which dendrimer has a structure in which no hemisphere of a notional sphere centred on M and containing the dendrimer is devoid of a said first single bond.

In formula (I), when X is a mono-dentate coordinating group, b is 1; when X is a bi-dentate coordinating group, b is 2; and when X is a tri-dentate coordinating group, b is 3.

The present invention also provides an organic light-emitting device comprising, in sequence, layers of a substrate, an electrode, a first optional charge-transporting layer, a light-emissive layer, a second optional charge-transporting layer and a counter electrode, wherein at least one of the light-emissive layer, first optional charge-transporting layer and second optional charge-transporting layers is a film comprising an organometallic dendrimer according to the invention.

Preferably the light-emissive layer is a film comprising an organometallic dendrimer according to the invention.

The film comprising the organometallic dendrimer may contain one or more additional species, which may comprise light-emitting dopants, charge-transporting species and/or additional molecular, dendritic and/or polymeric materials.

DETAILED DESCRIPTION OF THE INVENTION

The present invention is directed towards controlling intermolecular core-core interactions of organometallic cored dendrimers by controlling the number of dendrons attached to the core and their spatial distribution and the use of these dendrimers in OLEDs.

In a first embodiment of the invention, the required spatial distribution of dendrons, such that no hemisphere of a notional sphere centred on M and containing the dendrimer is devoid of a said first single bond (i.e. a single bond connecting CORE to a branching group or branching atom of DENDRITE), is achieved by ensuring that two or more dendrons are attached to each of two or more ligands X complexed to the metal cation. Thus the dendrimers are of formula (II):

$$\text{M-[X(DENDRITE(-Q)}_a)_y]_xY_z \qquad (II)$$

in which x represents an integer of 2 or more, y represents an integer of 2 or more, and the other symbols are as defined above for formula (I).

In a second embodiment of the invention, the organometallic dendrimers contain one or more dendrons attached to each of two or more ligands X complexed to the metal cation in an arrangement that distributes the dendrons more evenly around the metal containing core. When the dendrons are attached to the same group of each ligand, the dendrimers of this embodiment are preferably meridinal (rather than facial) for complexes in which the ligands are attached to the metal cation with an octahedral geometry, and trans (rather than cis) for complexes in which the ligands are attached to the metal cation with a square planar geometry. For example, in dendrimers that contain iridium (III) as part of the core, 2-phenylpyridine ligands attached to the metal cation could have all the dendrons attached to the phenyl rings. Given that it is important to control the intermolecular interactions it is preferable to have the dendrons on at least two of the ligands and more preferably on all the ligands. It is also possible to have meridinal and trans arrangements about the metal complex at the core of the dendrimer when two or more dendrons are attached to the ligand. Another aspect of the invention in controlling intermolecular interactions is to have a combination of ligands around the metal cation that forms part of the core in which the dendrons are attached to different parts of the ligands. For example with a fac-iridium (III) complex as part of the dendrimer core the attachment of the dendrons could be so that one dendron is on a pyridyl ring of one 2-phenylpyridyl ligand and the other two dendrons are attached to the phenyl rings of the other two 2-phenylpyridyl ligands. A combination of ligands that have one dendron and two or more dendrons can be used.

It is sometimes possible, e.g. in square planar complexes, to divide the notional sphere containing the dendrimer in such a way that the said first single bonds (i.e. the single bonds connecting CORE to a branching group or branching atom of DENDRITE) all lie within the plane at which the two resulting hemispheres meet. It is to be understood that, in the context of the present invention, such hemispheres are not "devoid of a said first single bond". Thus, for example, dendrimers containing only two said first single bonds in a trans square planar arrangement about M are not excluded by the requirement that no hemisphere of the notional sphere is devoid of a said first single bond. On the other hand, dendrimers containing only two said first single bonds in a cis square planar arrangement about M are excluded by this requirement, because the notional sphere may be divided in such a way that one hemisphere contains both said first single bonds and the other hemisphere is devoid of a said first single bond.

FIG. 11 shows a schematic representation of some metal centered dendrimers in which the arrangement of dendrons, D, is such that the dendrimers either do, namely in B and Y, or do not, namely in A and X, satisfy the requirements of the current invention. The diagram has been simplified to show the symmetry and does not show the ligands that will be bonded to the metal and to which the dendrons are attached. In each case the illustration shows a notional sphere containing the dendrimer and the notional sphere is divided into an example set of hemispheres. For both A and X it can be seen that one of the hemispheres does not contain any single bonds to the dendrons, and hence these are not covered by the current invention. In B both hemispheres contain dendrons, and no hemisphere can be chosen that does not contain a dendron, hence these are covered by the current invention. Y illustrates the limiting case discussed above where the single bonds lie within the plane at which the two hemispheres meet; the difference between X and Y is, though, clearly apparent.

In all of the embodiments of the invention, one or more surface groups may be attached at distal ends of the dendrons.

The core of the dendrimers terminates at the first single bond attached to a branching group or branching atom of the dendron. Typically the branching group or branching atom is an aryl or heteroaryl group or N to which more than one branching chain is attached. The ligands attached to the metal cation must be such that the co-ordination requirements of the metal cation are fulfilled and the organometallic dendrimer is neutral, i.e., no extra counter-anions are required to balance the charge of the dendrimer. The presence of counter-anions can be detrimental to device performance.

The metal cation chosen can give rise to fluorescent or phosphorescent dendrimers although phosphorescent dendrimers are preferred. Phosphorescence can be observed from metal complexes of some d and f block elements and dendrimers based on iridium, platinum, and rhenium are preferred. Rhodium may also be used.

The ligands attached to the metal can be mono-, di- or tri-dentate with bi-dentate being preferred.

It is to be understood that, in the context of the present invention, an organometallic dendrimer is one in which at least one organic ligand is coordinated to the metal. Such dendrimers do not necessarily contain a metal-carbon bond, because the organic ligand may be coordinated to the metal through an atom other than carbon, e.g. a nitrogen atom. However, dendrimers which contain at least one metal-carbon bond are preferred. Preferably at least one of the dendrons is attached to a ligand that is bonded to the metal via at least one metal-carbon bond. For example the dendron may be attached to a ligand that is part of a cyclometallated ring.

The dendrimers are preferably of the type disclosed in PCT/GB02/00750 or in co-pending UK patent application No. 0206356.8, to which reference should be made for further details, but possessing at least two DENDRITE groups and satisfying the requirement that no hemisphere of a notional sphere centred on M and containing the dendrimer is devoid of a said first single bond.

Each DENDRITE, which may be the same or different, preferably represents an inherently at least partially conjugated dendritic molecular structure comprising aryl and/or heteroaryl groups or nitrogen and, optionally, vinyl or acetylenyl groups connected via $sp^2$ or sp hybridised carbon atoms of said (hetero)aryl, vinyl and acetylenyl groups or via single bonds between N and (hetero)aryl groups, CORE terminating in the first single bond which is connected to an $sp^2$ hybridised (ring) carbon atom of the first (hetero)aryl group or nitrogen to which more than one at least partially conjugated dendritic branch is attached, said ring carbon atom or N forming part of said DENDRITE.

In this context an inherently at least partially conjugated dendritic structure is one in which there is conjugation between the groups making up the dendritic structure, but the π system is not necessarily fully delocalised. The delocalisation of the π system is dependent on the regiochemistry of the attachments. Such dendritic structures can also be termed conjugated dendritic structures.

In one embodiment, at least one DENDRITE represents a dendritic molecular structure comprising at least one nitrogen atom which forms part of an aromatic ring system or is directly bonded to at least two aromatic groups, e.g. of the type described in co-pending UK patent application No. 0206356.8, CORE terminating in the single bond to the first nitrogen atom or aromatic ring to which more than one dendritic chain is attached, said nitrogen atom or ring forming part of said DENDRITE.

In a preferred embodiment the dendrimers are of formula (III):

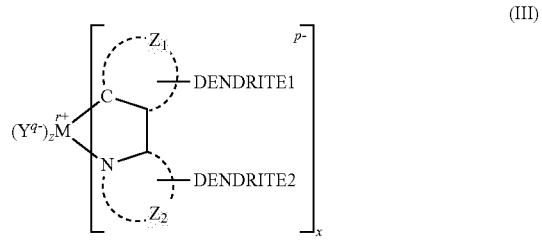

in which M is a metal cation with formal charge r+, $Z_1$ and $Z_2$ are groups required to complete 5 or 6 membered aryl or heteroaryl rings which can be optionally substituted, DENDRITE1 and DENDRITE2 are dendrons, Y is a neutral or anionic ligand, and each Y can be the same or different if z is greater than 1, x is an integer of 1 or more, z is 0, 1, 2, or 3, and the dendrimer is neutral such that r=(p.x)+(q.z). Preferably x is 2 or 3.

It is preferred that $Z_1$ is such that the 5 or 6 membered aryl or heteroaryl ring which can optionally be part of a fused ring system is selected from phenyl, pyridyl, thiophenyl, naphthyl, anthryl, phenanthryl, benzamidazolyl, carbazolyl, fluorenyl, pyrimidinyl, pyrazinyl, pyridazinyl, quinolinyl, isoquinolinyl, quinoxalinyl, benzothiophenyl, phthalazinyl, quinazolinyl, imidazolyl, pyrazolinyl, oxazolinyl, oxadiazolinyl, triazolyl, triazinyl, thiadiazolyl, benzimidazolyl, benzoxazolyl, phenanthridinyl, furyl and benzothiophenyl. It is preferred that $Z_2$ is such that the 5 or 6 membered aryl or heteroaryl ring which can optionally be part of a fused ring system is selected from pyridine, pyrimidine, pyrazine, pyridazine, quinoline, isoquinoline, quinoxaline, phthalazine, quinazoline, naphtholidine, cinnoline, pyrimidine, phenanthroline, imidazole, pyrazole, oxazole, oxadiazole, triazole, thiadiazole, benzimidazole, benzoxazole, benzthiazole and phenanthridine. Suitable optional substituents on the (hetero)aryl rings include halo, alkyl (C1 to 15), haloalkyl (e.g. $CF_3$, $CF_2CF_3$), alkyloxy, aryloxyaryl, alkyloxyaryl, aryl, alkylaryl, cyano, amino, dialkylamino, diarylamino, allylthio, arylthio, sulfinyl, sulfonyl, aryloxy, alkylarylamino, benzylic alcohol and aldehyde.

Preferred ligands Y include ligands of formula (IV):

in which $Z_1$ and $Z_2$ are as defined above and * represents a bond to M. Other preferred ligands Y include β-diketonates, 2-carboxylpyridines, such as picolinic acid, triarylphosphines, such as triphenylphosphine, trialkylphosphines, ethylenediamine, cyanide, carbon monoxide and carbon monosulfide.

The dendrons can comprise non-conjugated units, a combination of conjugated and non-conjugated units, e.g. as in Fréchet type dendrons, or conjugated units. A dendrimer that contains more than one dendron can have a combination of these types although conjugated dendrons are preferred. Preferably at least one conjugated dendron is present. It is also further preferred that two or more ligands have conjugated dendrons attached and it is further preferred that all the ligands have conjugated dendrons attached. Preferably the dendrons do not contain oxygen atoms in the linking units, although oxygen atoms may be present in the surface groups.

The conjugated dendrons comprise branching and optionally linking units. Branching groups have three or more attachments. The branching units can be aryl and/or heteroaryl units and/or a nitrogen atom. Linking units can be aryl, heteroaryl, vinyl or acetylenyl. The aryl or heteroaryl units can be fused ring systems. When conjugated dendrons are used, different bonding arrangements and/or generation can be used so that asymmetric dendrimers are formed. Commonly it is advantageous for dendrimers to be second generation or higher. However, for the dendrimers of this invention, in which the dendrons are more evenly distributed around the core, many of the advantages of high generation dendrimers can be achieved at a lower generation, which simplifies synthesis of the materials.

The organometallic dendrimers with conjugated dendrons can be formed in two main ways. The dendron can be attached to the ligand and then the ligand can be attached to the metal cation in the desired arrangement for the organometallic dendrimers herein described as part of the invention. Alternatively the ligand or ligands with suitable reactive moieties which may be the same or different can be complexed to the metal cation and the complex so formed can then be reacted with one or more dendrons with suitable reactive functionality at their foci. When the ligand or dendron contains a halide such as bromine or iodine the complementary component can contain a group such as a boronic acid, boronate ester, stannane, or vinylic or acetylenyl group such that the two can be coupled using palladium catalysis. Where more than one dendron is attached to a ligand in the final dendrimer one or more can be added to the ligand before complexation to the metal cation with the remaining dendrons being added after complexation to a point of the ligand that carries a suitable reactive moiety.

In a preferred embodiment the organometallic dendrimers are capable of emitting visible light. In an alternative embodiment the organometallic dendrimers have charge-transporting properties. It should be noted that the dendrimers that emit light can also transport charge. Also some organometallic dendrimers can emit light at wavelengths suitable for optical communications.

The surface groups Q are preferably of the type disclosed in PCT/GB02/00750, to which reference should be made for further details. Suitable surface groups include branched and unbranched alkyl, especially t-butyl, branched and unbranched alkoxy, for example 2-ethylhexyloxy, hydroxy, alkylsilane, carboxy, carbalkoxy, and vinyl. A more comprehensive list includes a further-reactable alkene, (meth)acrylate, sulphur-containing, or silicon-containing group; sulphonyl group; polyether group; $C_1$-to-$C_{15}$ alkyl (preferably t-butyl) group; amine group; mono-, di- or tri-$C_1$-to-$C_{15}$ alkyl amine group; —COOR group wherein R is hydrogen or $C_1$-to-$C_{15}$ alkyl; —OR group wherein R is hydrogen, aryl, or $C_1$-to-$C_{15}$ alkyl or alkenyl; —$O_2$SR group wherein R is $C_1$-to-$C_{15}$ alkyl or alkenyl; —SR group wherein R is aryl, or $C_1$-to-$C_{15}$ alkyl or alkenyl; and —$SiR_3$ group wherein the R groups are the same or different and are hydrogen, $C_1$-to-$C_{15}$ alkyl or alkenyl, or —SR' group (R' is aryl or $C_1$-to-$C_{15}$ alkyl or alkenyl), aryl, or heteroaryl. Typically t-butyl and alkoxy groups are used. Different surface groups may be present on different dendrons or different distal groups of a dendron. The distal groups of the dendron to which the surface groups are attached are preferably (hetero)aryl groups. Where t-butyl groups are the surface groups attached to phenyl rings it is preferable that more than one is attached to each of the distal phenyl units.

The surface groups of the organometallic dendrimers are generally selected so that the dendrimer blend is soluble in solvents suitable for solution processing, e.g. THF, toluene, chloroform, chlorobenzene, xylenes and alcoholic solvents such as methanol. The surface groups can also be chosen such that the dendrimer can be patterned. For example, a crosslinkable group can be chosen, which can be crosslinked upon irradiation or by chemical reaction. Alternatively, the surface groups can comprise protecting groups that can be removed to leave crosslinkable groups.

The properties of dendrimers make them ideal for solution processing. The dendrimers can be dissolved in a solvent, the solution deposited onto a substrate, and the solvent removed to leave a solid film. Conventional solution-processing techniques can be used, for example spin-coating, printing (e.g. ink-jet printing) and dip-coating. A solid film containing the organometallic dendrimers can be either fluorescent or phosphorescent. The solid film is preferably formed on one side of a substrate and the thickness of the solid film is preferably less than 2 microns.

The present invention also provides an OLED incorporating a solid film comprising one or more of the organometallic dendrimers. In its simplest form, an organic light-emitting or electroluminescent device can be formed from a light-emitting layer sandwiched between two electrodes, at least one of which is transparent to the emitted light. Often there are one or more hole-transporting layers between the anode and the light-emitting layer and/or one or more electron-transporting layers between the light-emitting layer and the cathode. In one preferred embodiment the film comprising the organometallic dendrimer forms the light-emitting layer in an OLED. It is particularly preferred that the dendrimers are the light-emitting species in this light-emitting layer. In an alternative embodiment the film comprising the organometallic dendrimer forms a charge-transporting layer in an OLED.

Such a device can have a conventional arrangement comprising a transparent substrate layer, e.g. a glass or PET layer, a transparent electrode layer, a light-emitting layer and a second electrode. The anode, which is generally transparent, is preferably made from indium tin oxide (ITO) although other similar materials including indium oxide/tin oxide, tin oxide/antimony, zinc oxide/aluminium, gold and platinum can also be used, as can conducting polymers such as PANI (polyaniline) or PEDOT/PSS. The cathode is normally made of a low work function metal or alloy such as Al, Ca, Mg, Li or MgAl or optionally with an additional layer of LiF. In an alternative configuration, the substrate may be made of an opaque material such as silicon and light is emitted through the opposing electrode. The OLED devices may be actively or passively addressed.

For a typical OLED device, as described above where the organometallic dendrimer is emissive, a solution containing the organometallic dendrimer can be applied over a transparent electrode layer, the solvent evaporated and then subsequent charge-transporting layers can be applied. The thickness of the dendrimer layer in the OLED is typically 10 nm to 1000 nm, preferably no more than 200 nm, more preferably 30 nm to 120 nm. When a hole transport layer is incorporated between the anode and the emissive organometallic dendrimer containing layer the hole transport material must not be removed to a significant extent during the solution deposition.

An OLED device incorporating an emissive layer comprising the organometallic dendrimer may optionally have an adjacent first and/or second charge-transporting layer. In our work on organometallic dendrimers, it has been found that it is particularly beneficial to have a hole-blocking/electron-transporting layer between the light-emitting dendrimer layer and the cathode. Suitable materials for such a hole-blocking/electron-transporting layer are known and include 2,9-dimethyl-4,7-diphenyl-1,10-phenanthroline (BCP), 1,3,5-tris[2-N-phenylbenzimidazol)benzene (TPBI), 2-biphenyl-5(4'-t-butylphenyl)oxadiazole (PBD), aluminium tris(8-hydroxyquinolate) (Alq), and aluminium bis(2-methyl-8-quinolato)-4-phenylphenolate (BAlq).

Furthermore, additional emissive (fluorescent or phosphorescent) or charge-transporting species may optionally be added to the layer of the organometallic dendrimers to improve device characteristics, e.g. efficiency and lifetime. It may further be of benefit to include one or more other molecular and/or dendrimeric and/or polymeric species in the blend of dendrimers to give improved performance. In one embodiment such additional components form a part of the total blend from 95 to 5 mol %. In another embodiment the additional components form greater than 50%, more preferably greater than 70%, by weight of the blend. In that embodiment it is preferred that the additional molecular, dendritic or polymeric species can transport charge in their own right, for example a conjugated polymer or dendrimer. In a further embodiment the additional components form less than 50%, more preferably less than 30%, by weight of the blend. For example, additional charge-transporting components for use with the light-emitting dendrimers include TPBI, PBD, BCP, 4,4'-bis(N-carbazole)biphenyl (CBP), 4,4',4"-tris(N-carbazolyl)triphenylamine (TCTA), and tris-4-(N-3-methylphenyl-N-phenyl)phenylamine (MTDATA), and substituted derivatives thereof.

Such dendrimers can also be used in other device applications such as photovoltaic cells which can contain one or more layers. When used in photovoltaic cells the dendrimers must be capable of absorbing light and/or transporting charge. The dendrimer may be used as a homogeneous layer in a photovoltaic device or blended with other molecular and/or dendritic and/or polymeric materials. The dendrimer may be used in one or more layers of the photovoltaic device.

The invention will be described in the examples that follow, with reference to the accompanying drawings, wherein:

EXAMPLE 1

A-1

Figure 1:
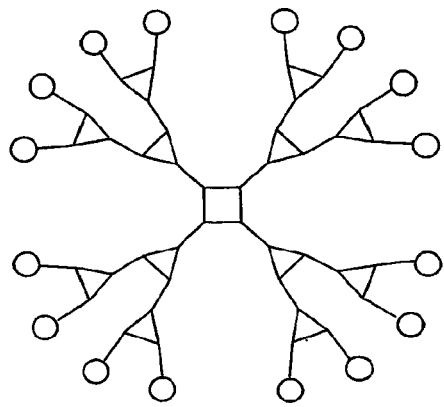
FIG. 1 shows a schematic diagram of a second generation dendrimer A and a higher-order (third generation) dendrimer B.
Figure 1:
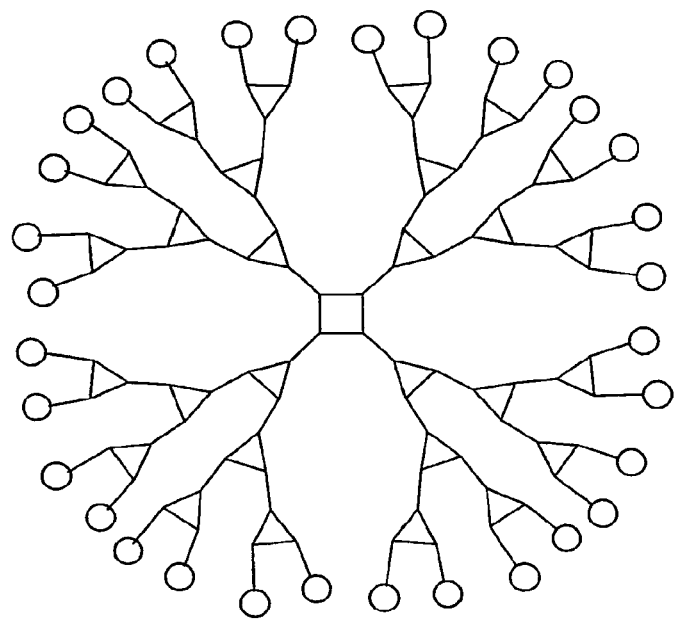
Figure 2:
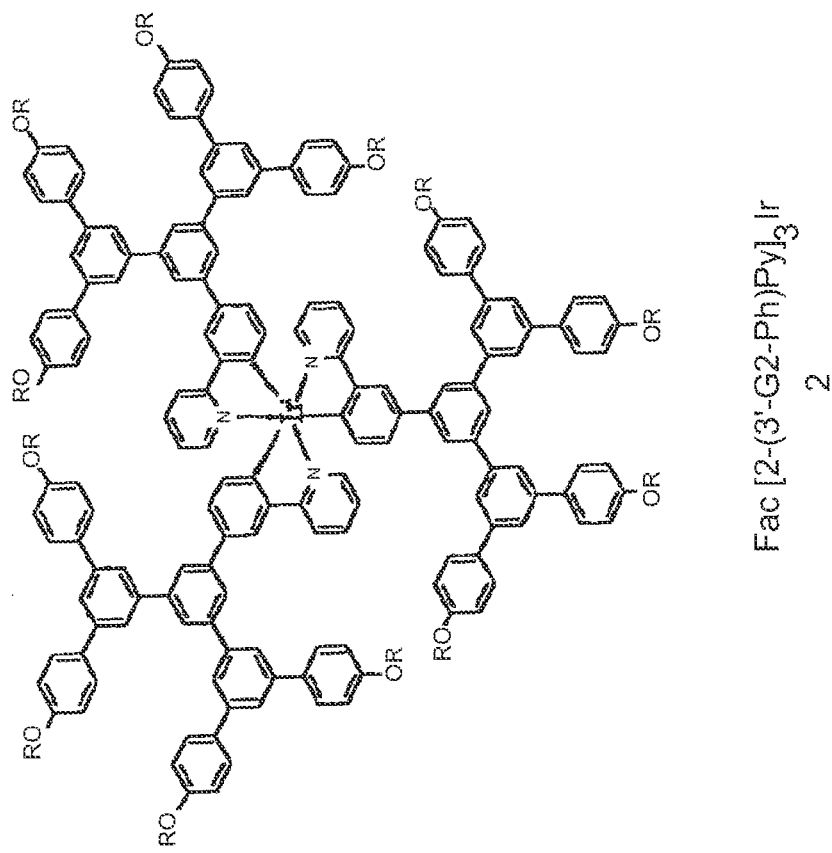
FIG. 2 shows first generation (1) and second generation (2) facial isomers of iridium based dendrimers with dendrons attached only to the phenyl rings of the ligands.
Figure 2:
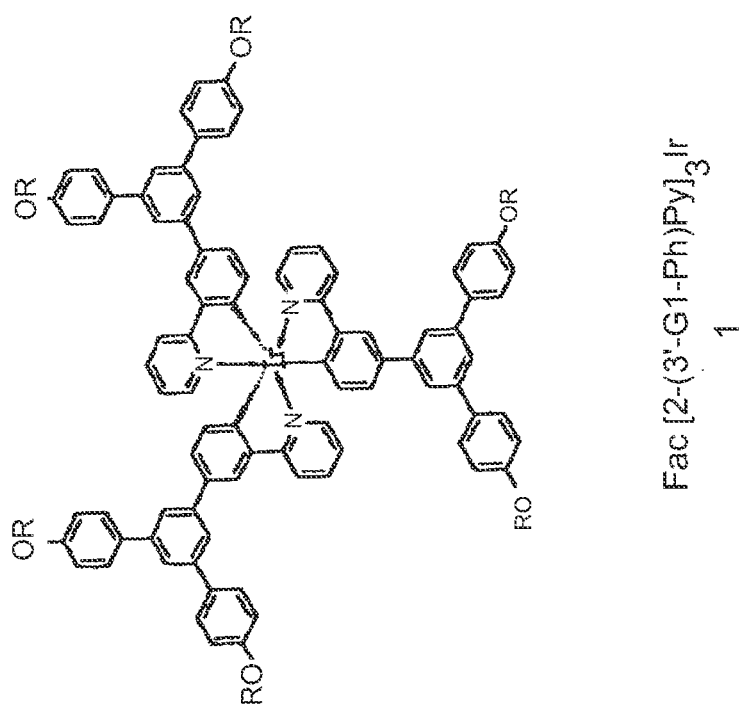
Figure 3:
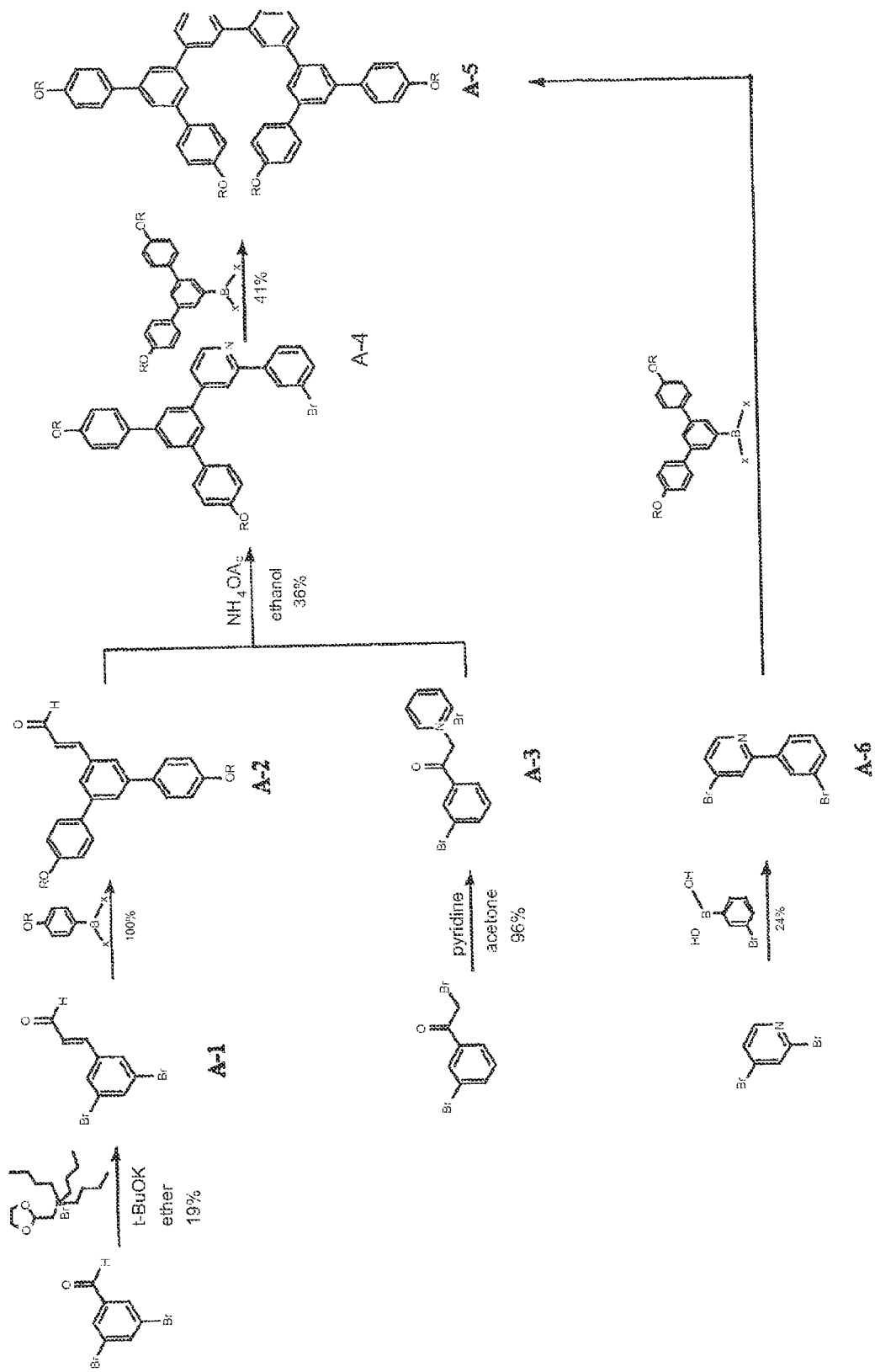
FIG. 3 shows a reaction scheme for the preparation of a first generation dendritic ligand in which dendrons are attached to both the phenyl and pyridine rings of a phenylpyridine ligand (Examples 1 to 6).
Figure 4:
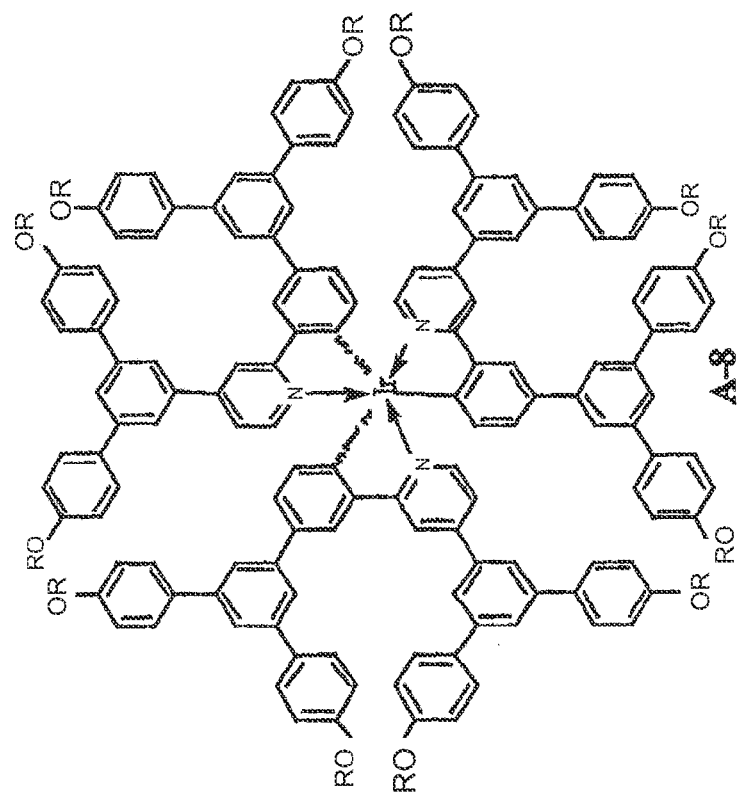
FIG. 4 shows a reaction scheme for two methods of the preparation of a first generation iridium dendrimer using the ligand prepared in FIG. 3. (One method is described in Example 7.)
Figure 4:
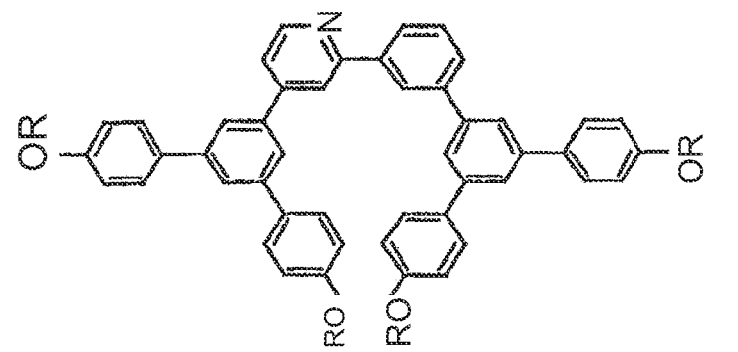
Figure 5:
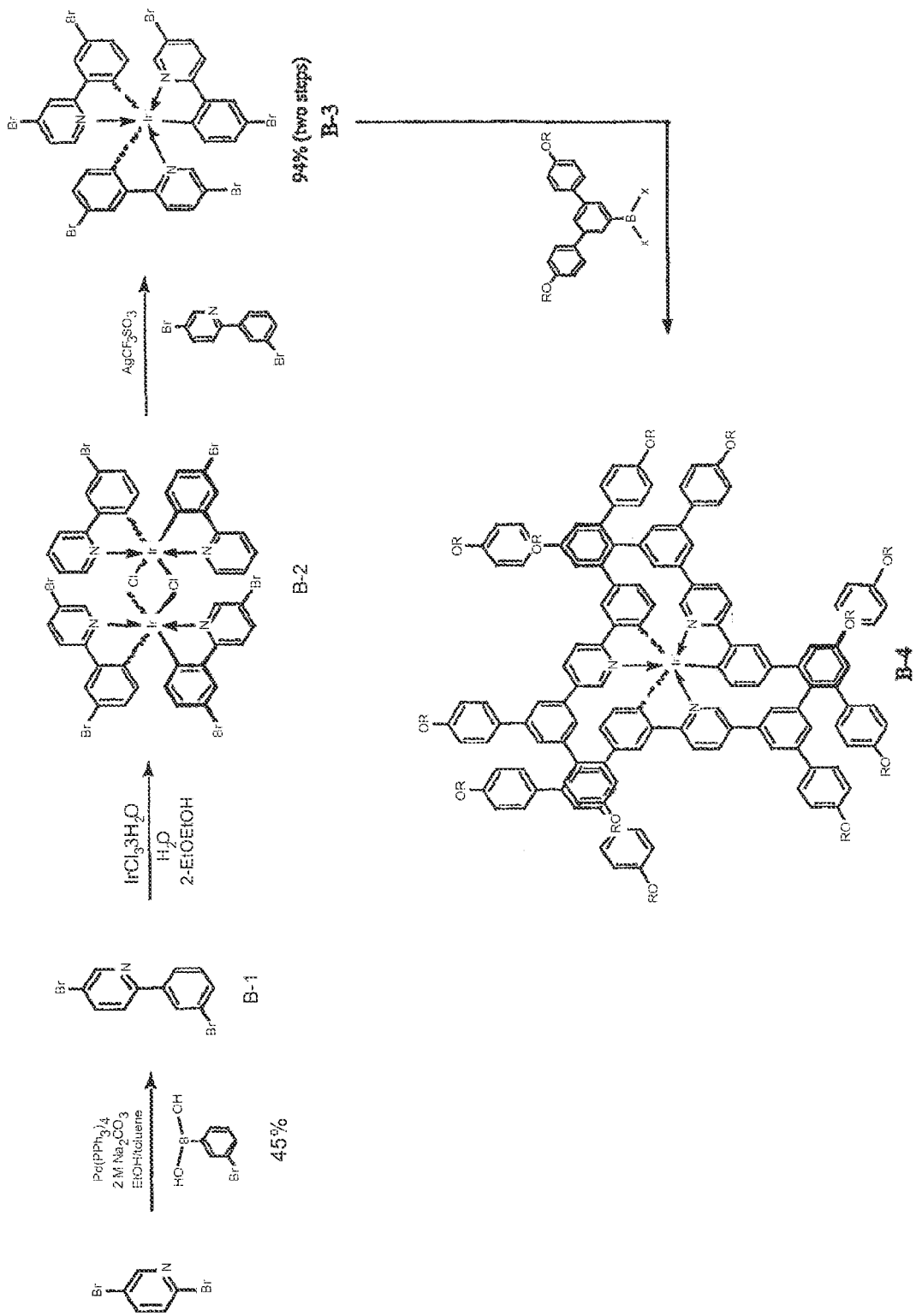
FIG. 5 shows an alternative reaction scheme for the preparation of a first generation iridium dendrimer B-4 (Examples 8 to 10).
Figure 6:
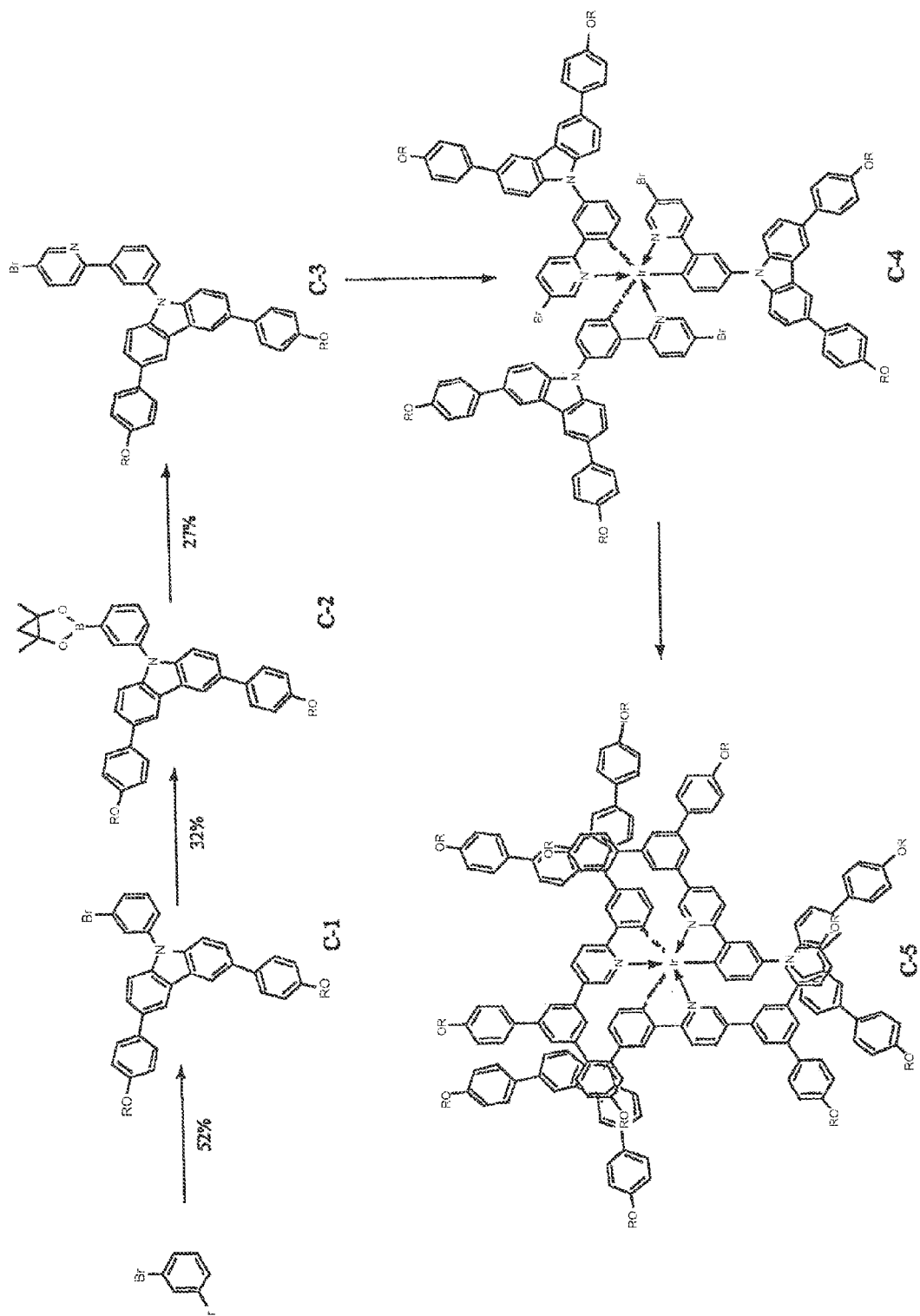
FIG. 6 shows a reaction scheme for the preparation of first generation iridium dendrimers containing more than one kind of dendron (Examples 11 to 14).

3-(3',5'-dibromophenyl)-2-propenal 3,5-dibromobenzaldehyde (16.1 g, 61.0 mmol) was added to a cold (ice-water bath) solution of tert-butoxide (13.0 g, 116 mmol), (1,3-dioxolan-2-ylmethyl)tri-n-butylphosphine bromide salt (4.5 M, 32 cm$^3$, 144 mmol) in 400 cm$^3$ of ether under argon. The mixture was stirred at 0-2° C. for 2 h. 1.0 M HCl$_{(aq)}$ (300 cm$^3$) was added to the mixture. The reaction was gradually warmed to room temperature and stirred at room temperature for 21 h. The two layers were separated. The aqueous layer was extracted with ether (3×200 cm$^3$). The organic layer and the ether extracts were combined, washed with brine (1×300 cm$^3$) and dried over anhydrous magnesium sulfate. The solvents were completely removed to leave a yellow solid. The solid was purified by column chromatography of silica gel using ethyl acetate-light petroleum (40-60° C.) as eluent to give 3.36 g (19%) of A-1 as a colourless solid; $\delta_H$(200 MHz; CDCl$_3$) 6.68 (1 H, dd, J 7.4 & 16 Hz, vinylH), 7.33 (1 H, d, J 16 Hz, vinylH), 7.33 (2 H, m, ArH), 7.63 (1 H, m, ArH), and 9.72 (1 H, d, J 7.6 Hz, CHO); m/z [CI(NH$_3$)] 306, 308, 310 (MNH$_4^+$), and 288, 290, 292 (M$^+$).

EXAMPLE 2

A-2

3-{3',5'-Di[4"-(2'"-ethylhexyloxy)phenyl]phenyl}-2-propenal

A mixture of the boronic compound G0-BX$_2$ prepared in accordance with Example 4 of PCT/GB02/00739 (647 mg, 2.59 mmol), 3-(3',5'-dibromophenyl)-2-propenal A-1(326 mg, 1.24 mmol), tetrakis(triphenylphosphine) palladium (0) (91 mg, 0.079 mmol), 2 M Na$_2$CO$_{3(aq)}$ (1.0 cm$^3$), EtOH (1.0 cm$^3$) and toluene (3.5 cm$^3$) was degassed and then heated at reflux (with bath temperature of 106° C.) under argon for 18 h. The mixture was allowed to cool to ambient temperature and then diluted with water (5 cm$^3$) and ether (6 cm$^3$). The two phases were separated. The aqueous layer was extracted with ether (3×5 cm$^3$). The organic layer and the ether extracts were combined, washed with brine (1×10 cm$^3$) and dried over anhydrous magnesium sulfate. The solvents were completely removed. The residue was purified by column chromatography over silica gel using DCM-light petroleum (0:1 to 1:30 and 1:10) as eluent to give 607 mg (100%) of A-2 as a light yellow oil; $\delta_H$(200 MHz; CDCl$_3$) 0.80-1.05 (12 H, m, Me), 1.24-1.64 (16 H, m, CH$_2$), 1.68-1.88 (2 H, m, CH), 3.91 (4 H, m, ArOCH$_2$), 6.84 (1 H, dd, J 7.8 & 16 Hz, vinylH), 7.20 (1 H, d, J 16 Hz, vinylH), 7.58 (4 H, m, ArH), 7.67 (2 H, m, ArH), 7.79 (1 H, m, ArH), and 9.77 (1 H, d, J 16 Hz, CHO); m/z [APCI$^+$] (MH$^+$).

EXAMPLE 3

A-3

Pyridine (6 cm$^3$) was added to a mixture of 3-bromophenylacylbromide (956 mg, 3.44 mmol) and 44 cm$^3$ of acetone. The reaction was stirred at room temperature for 2 h and the solvent was removed under reduced pressure. The resulting precipitate was washed with ether (4×10 cm$^3$) and dried under reduced pressure to leave 1.18 g (96%) of A-3 as a light pink/cream solid.

EXAMPLE 4

A-4

2-(3'-Bromophenyl)-4-{3",5"-di[4'"-(2""-ethylhexyloxy)phenyl]phenyl}-pyridine Ammonium acetate (5.97 g, 77.5 mmol) was added to a mixture of the 3-{3',5'-di[4"-(2'"-ethylhexyloxy)phenyl]phenyl}-2-propenal (607 mg, 1.12 mmol), the pyridinium salt A-3 (481 mg, 1.35 mmol) and 12 cm$^3$ of ethanol. The mixture was stirred and heated at a 90° C. oil bath for 5 h under argon. The mixture was diluted with water (10 cm$^3$) and extracted with DCM (4×15 cm$^3$). The DCM extracts were combined, washed with brine (1×30 cm$^3$), dried (Na$_2$SO$_4$) and the solvent was removed to leave a light brown oil. The oil was purified by column chromatography over silica gel using DCM-light petroleum (0:1 to 1:40) as eluent to give 292 mg (36%) of A-4 as a light yellow oil; $\delta_H$(200 MHz; CDCl$_3$) 0.78-1.04 (12 H, m, Me), 1.17-1.64 (16 H, m, CH$_2$), 1.67-1.88 (2 H, m, CH), 3.92 (4 H, m, ArOCH$_2$), 7.01 (4 H, m, ArH), 7.08-8.03 (13 H, m, ArH & PyH), 8.25 (1 H, m, ArH), and 8.78 (1 H, m, PyH); m/z [APCI$^+$] 717, 718, 719, 720, 721, 722 (M$^+$).

EXAMPLE 5

A-5

4-{3',5'-Di[4"-(2'"-ethylhexyloxy)phenyl]phenyl}-2-(3""-{3""',5""'-di[4""''-(2""'''-ethylhexyloxy) phenyl] phenyl}phenyl)-pyridine A mixture of the boronic compound G1-BX$_2$ prepared in accordance with Example 6 of PCT/GB02/00739 (1.19 mg, 1.66 mmol), aryl bromide A-4 (1.14 g, 2.16 mmol), tetrakis (triphenylphosphine) palladium (0) (134 mg, 0.116 mmol), 2 M Na$_2$CO$_{3(aq)}$ (2.0 cm$^3$), EtOH (2.0 cm$^3$) and toluene (7 cm$^3$) was degassed and then heated at reflux (with bath temperature of 105° C.) under argon for 86 h. The mixture was allowed to cool to ambient temperature. The two layers were separated. The aqueous layer was extracted with ether (3×6 cm$^3$). The organic layer and the ether extracts were combined, washed with brine (1×18 cm$^3$) and dried over anhydrous sodium sulfate. The solvents were completely removed. The residue was purified by column chromatography over silica gel using DCM-light petroleum (0:1 to 1:10) as eluent to give 755 mg (41%) of A-5 as a light yellow oil; $\lambda_{max}$/nm (thin film) 270; $\delta_H$(200 MHz; CDCl$_3$) 0.80-1.08 (24 H, m, Me), 1.22-1.65 (32 H, m, CH$_2$), 1.69-1.91 (4 H, m, CH), 3.92 (8 H, m, ArOCH$_2$), 6.92-7.12 (8 H, m, ArH), 7.51-7.83 (16 H, m, PyH & ArH), 8.03-8.12 (3 H, m, PyH & ArH), 8.41 (1 H, m, ArH), and 8.83 (1 H, m, PyH); m/z [APCI$^+$] 1122, 1123, 1124, 1125, 1126 (M$^+$).

EXAMPLE 6

A-6

4-bromo-2-(3'-bromophenyl)-pyridine

A mixture of 2,4-dibromopyridine (3.30 g, 13.9 mmol), 3-bromophenylboronic acid (3.69 g, 16.7 mmol), tetrakis (triphenylphosphine) palladium (0) (643 mg, 0.557 mmol), 2 M Na$_2$CO$_{3(aq)}$ (12 cm$^3$), EtOH (12 cm$^3$) and toluene (40 cm$^3$) was degassed and then heated at reflux with a bath temperature of 110° C. under argon for 3.5 days. The reaction was allowed to cool and the two phases were separated. The aqueous layer was extracted with ether (3×13 cm$^3$). The organic layer and the ether extracts were combined, washed with brine (1×30 cm$^3$) and dried over anhydrous sodium sulfate. The solvents were completely removed to leave a black brown oil. The oil was purified by column chromatography over silica gel using DCM-light petroleum (0:1 to 1:10) as eluent to give 1.03 g (24%) of A-6 as a white solid; $\delta_H$(200 MHz; CDCl$_3$) 7.36 (1 H, m, ArH), 7.45 (1 H, m, PyH), 7.58 (1 H, m, ArH), 7.89 (2 H, m, PyH & ArH), 8.16 (1 H, m, ArH), and 8.52 (1 H, m, PyH); m/z [APCI$^+$] 311, 314, 316 (MH$^+$).

EXAMPLE 7

A-8

Fac tris[4-{3'5'-di[4"-(2'"-ethylhexyloxy)phenyl] phenyl}-2-(3""-{3""',5""'-di[4""''-(2""'''-ethylhexyloxy)phenyl]phenyl}phenyl)-pyridine]iridium (III)

A mixture of the ligand A-5 (200 mg, 0.178 mmol), Ir(acac)$_3$ (12.4 mg, 0.025 mmol) and glycerol (1 cm$^3$) was degassed and then heated with heating mantle at 220° C. for 14 h. The mixture was allowed to cool to ambient temperature. The mixture was dissolved into acetone (8 cm$^3$) and DCM (3 cm$^3$). The solution was left to stand and the layer containing the dendrimer was separated from the glycerol layer. The mixture was evaporated to about 4 cm$^3$ and purified by column chromatography over silica gel using light petroleum as eluent to give 9 mg (10%) of A-8 as a yellow orange solid; $\lambda_{max}$/nm (thin film) 277; $\delta_H$(400 MHz; CDCl$_3$) 0.87-1.02 (72 H, m, Me), 1.24-1.62 (96 H, m, CH$_2$), 1.69-1.83 (12 H, m, CH), 3.80-3.97 (24 H, m, ArOCH$_2$), 6.90-7.07 (24 H, m, ArH), 7.23 (3 H, m, PyH), 7.32-7.93 (51 H, m, ArH & PyH), 8.14 (3 H, m, PyH), and 8.34 (3 H, m, PyH); m/z [MALDI] 3560, 3561, 3562, 3563, 3564, 3565, 3567, 3568 (M$^+$).

EXAMPLE 8

B-1

5-bromo-2-(3'-bromophenyl)-pyridine

A mixture of 2,5-dibromopyridine (4.33 g, 17.7 mmol), 3-bromophenylboronic acid (4.70 g, 21.3 mmol), tetrakis (triphenylphosphine) palladium (0) (800 mg, 0.692 mmol), 2

M Na$_2$CO$_{3(aq)}$ (18 cm$^3$), EtOH (18 cm$^3$) and toluene (50 cm$^3$) was degassed and heated at reflux with a bath temperature of 105° C. under argon for 23 h. The reaction was allowed to cool and the two phases were separated. The aqueous layer was extracted with ether (3×15 cm$^3$). The organic layer and the ether extracts were combined, washed with brine (1×40 cm$^3$) and dried over anhydrous sodium sulfate. The solvents were completely removed to leave an orange oil. The oil was purified by column chromatography over silica gel using DCM-light petroleum (0:1 to 1:10) as eluent to give 2.50 g (45%) of B-1 as a pale yellow solid; δ$_H$(200 MHz; CDCl$_3$) 7.26-7.42 (1 H, m, ArH), 7.57 (2 H, m, PyH & ArH), 7.88 (2 H, m, PyH & ArH), 8.14 (1 H, m, ArH), and 8.74 (1 H, m, PyH); m/z [CI(NH$_3$)] 312, 314, 316 (MH$^+$).

EXAMPLE 9

B-3

Fac tris[5-bromo-2-(3'-bromophenyl)-pyridine]iridium (III)

A mixture of the 5-bromo-2-(3'-bromophenyl)pyridine (1.00 g, 3.20 mmol), iridium chloride tri-hydrate (250 mg, 0.709 mmol), H$_2$O (6.3 cm$^3$) and 2-ethoxyethanol (19 cm$^3$) was heated at reflux with a bath temperature of 127° C. under a nitrogen flow for 24 h before being cooled. A light orange yellow solid precipitated from the mixture. The liquid was removed from the mixture to leave a precipitate. The precipitate was washed with 90% of EtOH (3×10 cm$^3$) and then EtOH (1×10 cm$^3$). The solid was dried to give 656 mg of a yellow orange solid as the desired product and the excess ligand.
A mixture of the above yielded products (656 mg), 5-bromo-2-(3'-bromophenyl)-pyridine B-1 (696 mg, 2.22 mmol) and silver trifluoromethanesulfonate (220 mg, 0.856 mmol) was heated with a bath temperature of 160-163° C. for a week under argon. The reaction was then allowed to cool to room temperature to give a brown solid. The solid was purified by column chromatography over silica gel with ethyl acetate-light petroleum (0:1 to 1:20) as eluent to give 495 mg of the excess ligand, and then DCM-light petroleum (1:4 to 1:0) as eluent to give 753 mg (94% for two steps referring to iridium chloride tri-hydrate) of B-3 as a yellow powder; δ$_H$(200 MHz; CDCl$_3$) 6.55 (1 H, m, ArH), 6.95 (1 H, m, PyH), 7.54 (1 H, m, ArH), and 7.71-7.89 (3 H, m, ArH & PyH); m/z [APCI$^+$]1126, 1127, 1128, 1129, 1130, 1131, 1132 (MH$^+$).

EXAMPLE 10

B-4

Fac tris[5-{3',5'-di[4''-(2'''-ethylhexyloxy)phenyl]phenyl}-2-(3''''-{3''''',5'''''-di[4''''''-(2'''''''-ethylhexyloxy)phenyl]phenyl}phenyl)-pyridine] iridium (III)

A mixture of the boronic compound G1-BX$_2$ prepared in accordance with Example 6 of PCT/GB02/00739 (1.26 g, 0.858 mmol), tris[5-bromo-2-(3'-bromophenyl)pyridine] iridium (III) (178 mg, 0.158 mmol), tetrakis(triphenylphosphine) palladium (0) (36 mg, 0.032 mmol), 2 M Na$_2$CO$_{3(aq)}$ (1.0 cm$^3$), EtOH (1.0 cm$^3$) and toluene (3.0 cm$^3$) was degassed and then heated at reflux with a bath temperature of 105° C. under argon for 64 h. The mixture was allowed to cool. The mixture was purified by column chromatography over silica gel using DCM-light petroleum (0:1 to 1:30) as eluent and then chromatotron using DCM-light petroleum (1:30) as eluent to give 30 mg (5%) of B-4 as a orange solid; δ$_H$(200 MHz; CDCl$_3$) 0.77-1.08 (72 H, m, Me), 1.15-1.86 (108 H, m, CH$_2$ & CH), 3.69 (12 H, m, ArOCH$_2$), 3.89 (12 H, m, ArOCH$_2$), 6.68 (12 H, m, ArH), 7.00 (12 H, m, ArH), and 7.22-8.32 (60 H, m, ArH & PyH); m/z [MALDI] 3562, 3563, 3564, 3567, 3568 (M$^+$).

EXAMPLE 11

DEHP-Car 3,6-Di[4'-(2''-ethylhexyloxy)phenyl]carbazole

A mixture of 3,6-dibromocarbazole (12.0 g, 37.1 mmol), the boronic compound G0-BX$_2$ prepared in accordance with Example 4 of PCT/GB02/00739 (24.1 g, 96.4 mmol), tetrakis (triphenylphosphine) palladium (0) (800 mg, 0.692 mmol), 2 M Na$_2$CO$_{3(aq)}$ (40 cm$^3$), EtOH (40 cm$^3$) and toluene (100 cm$^3$) was degassed and then heated at reflux (with bath temperature of 100° C.) under argon for 42 h. The mixture was allowed to cool and diluted with H$_2$O (30 cm$^3$) and ether (40 cm$^3$). The two layers were separated. The aqueous layer was extracted with ether (3×40 cm$^3$). The organic layer and the ether extracts were combined, washed with brine (1×50 cm$^3$) and dried (Na$_2$SO$_4$) and filtered. The solvents were completely removed and the residue was purified by column chromatography over silica using ethyl acetate-light petroleum (0:1 to 1:10) and DCM-ethyl acetate-light petroleum (4:1:20) as eluent to give 14.7 g (69%) of DEHP-Car; m/z [APCI$^+$] 576 (M$^+$).

EXAMPLE 12

C-1

3-{3',6'-Di[4''-(2'''-ethylhexyloxy)phenyl]carbazolyl}phenyl bromide

Tris(dibenzylideneacetone)di-palladium (0) [Pd$_2$(dba)$_3$] (198 mg, 0.217 mmol) and tri-tert-butylphosphine (10% in hexane, 4.4 cm$^3$) were added to a degassed (Schlenk line, evacuated and then back-filled with argon) mixture of 3,6-di [4'-(2''-ethylhexyloxy)phenyl]carbazole DEHP-Car (2.50 g, 4.34 mmol), 1-bromo-3-iodobenzene (4.91 g, 17.4 mmol), sodium tert-butoxide (834 mg, 8.68 mmol), and distilled toluene (12 cm$^3$). The mixture was degassed again before being heated at reflux with bath temperature of 110° C. under argon for 63 h. The resultant was allowed to cool to room temperature and diluted with H$_2$O (20 cm$^3$) and ether (25 cm$^3$). The two phases were separated. The aqueous layer was extracted with ether (3×20 cm$^3$). The organic layer and the ether extracts were combined, washed with brine (1×40 cm$^3$) and dried over anhydrous sodium sulfate. The solvents were completely removed to leave an orange oil. The mixture was purified by column chromatography over silica gel using DCM-light petroleum (0:1 to 1:10) as eluent to give 1.65 g (52%) of C-1 as a light orange oil; δ$_H$(200 MHz; CDCl$_3$)

0.80-1.06 (12 H, m, Me), 1.26-1.68 (16 H, m, CH$_2$), 1.71-1.89 (2 H, m, CH), 3.93 (4 H, m, ArOCH$_2$), 7.04 (4 H, m, ArH), 7.42-7.74 (11 H, m, ArH & CarH), 7.80 (1 H, m, ArH), and 8.33 (2 H, m, CarH); m/z [APCI$^+$] 730, 731, 732, 733, 734 (MH$^+$).

EXAMPLE 13

C-2

2-(3-{3',6'-Di[4'''-(2''''-ethylhexyloxy)phenyl]carbazolyl}phenyl)-(4,4,5,5-tetramethyl-1,3,2-dioxaborolane)

Tert-butyl lithium (1.7 M, 2.1 cm$^3$, 3.59 mmol) was added to a cold (dry-ice/acetone bath) solution of aryl bromide C-1 (1.64 g, 2.24 mmol) in 13 cm$^3$ of anhydrous THF under an argon atmosphere. The mixture was stirred at −78° C. for 1 h and then 2-isopropoxy-4,4,5,5-tetramethyl-1,3,2-dioxaborolane (0.9 cm$^3$) was added rapidly to the cold mixture. The reaction was stirred at −78° C. for 2 h before being removed from the dry-ice/acetone bath. The mixture was then stirred at room temperature for 18 h and then quenched with H$_2$O (8 cm$^3$). The two phases were separated. The aqueous layer was extracted with ether (3×10 cm$^3$). The organic layer and the ether extracts were combined, washed with brine (1×30 cm$^3$) and dried over anhydrous sodium sulfate and the solvents were completely removed. Purification by column chromatography over silica gel using DCM-light petroleum (0:1 to 1:0) as eluent gave 554 mg (32%) of C-2 as a light brown oil; δ$_H$(200 MHz; CDCl$_3$) 0.83-1.03 (12 H, m, Me), 1.24-1.68 (28 H, m, CH$_2$ & Me), 1.68-1.88 (2 H, m, CH), 3.92 (4 H, m, ArOCH$_2$), 7.03 (4 H, m, ArH), 7.40-8.04 (12 H, m, CarH & ArH), and 8.33 (2 H, m, CarH); m/z [APCI$^+$] 776, 777, 778, 779, 780 (M$^+$).

EXAMPLE 14

C-3

4-Bromo-2-(3'-{3'',6''-di[4'''-(2''''-ethylhexyloxy)phenyl]carbazolyl}phenyl)pyridine A mixture of the bororate C-2 (500 mg, 0.643 mmol), 2,4-dibromopyridine (152 mg, 0.643 mmol), tetrakis(triphenylphosphine) palladium (0) (52 mg, 0.045 mmol), 2 M Na$_2$CO$_{3(aq)}$ (0.8 cm$^3$), EtOH (0.8 cm$^3$) and toluene (2 cm$^3$) was degassed and then heated at reflux with a bath temperature of 110° C. under argon for 45 h. The mixture was allowed to cool. The two phases were separated. The aqueous layer was extracted with ether (3×4 cm$^3$). The organic layer and the ether extracts were combined, washed with brine (1×7 cm$^3$) and dried over anhydrous sodium sulfate and the solvents were completely removed. Purification by column chromatography over silica gel using DCM-light petroleum (0:1 to 1:0) as eluent gave 140 mg (27%) of C-3 as a light brown solid; δ$_H$(200 MHz; CDCl$_3$) 0.82-1.07 (12 H, m, Me), 1.23-1.68 (16 H, m, CH$_2$), 1.69-1.88 (2 H, m, CH), 3.93 (4 H, m, ArOCH$_2$), 7.04 (4 H, m, ArH), 7.43-7.83 (11 H, m, CarH & ArH), 7.97 (1 H, m, PyH), 8.11 (1 H, m, PyH), 8.36 ((2 H, m, CarH), and 8.54 (1 H, m, PyH); m/z [APCI$^+$] 805, 806, 807, 808, 809 (M$^+$).

EXAMPLE 15

Photophysical and Device Properties

The photoluminescence quantum yields (PLQYs) of thin films of A-8 and B-4 were measured and found to be 32% and 70% respectively. This should be compared to the PLQYs of first, IrppyD1, (22%) and second, IrppyD2, (31%) generation dendrimers that have the same dendrons attached to only the same position of the phenyl ring of the ligand (J. P. J. Markham, et al *Appl. Phys. Lett.*, 2002, 80, 2645). That is, putting a second first generation dendron onto the ligands improves the PLQY by 50-140%. This demonstrates that the invention controls the undesirable intermolecular interactions. A further demonstration of this is that the PLQY of a solution of B-4 in toluene is 75%, which is comparable to the thin film PLQY, and shows that there is very little quenching of luminescence in the solid state. Given the relative difficulty of synthesising higher generations this is a significant improvement on the prior art. A further practical advantage is that the dendrimers do not need blending with a host material to have a high PLQY and high EL device efficiency.

Figure 7:
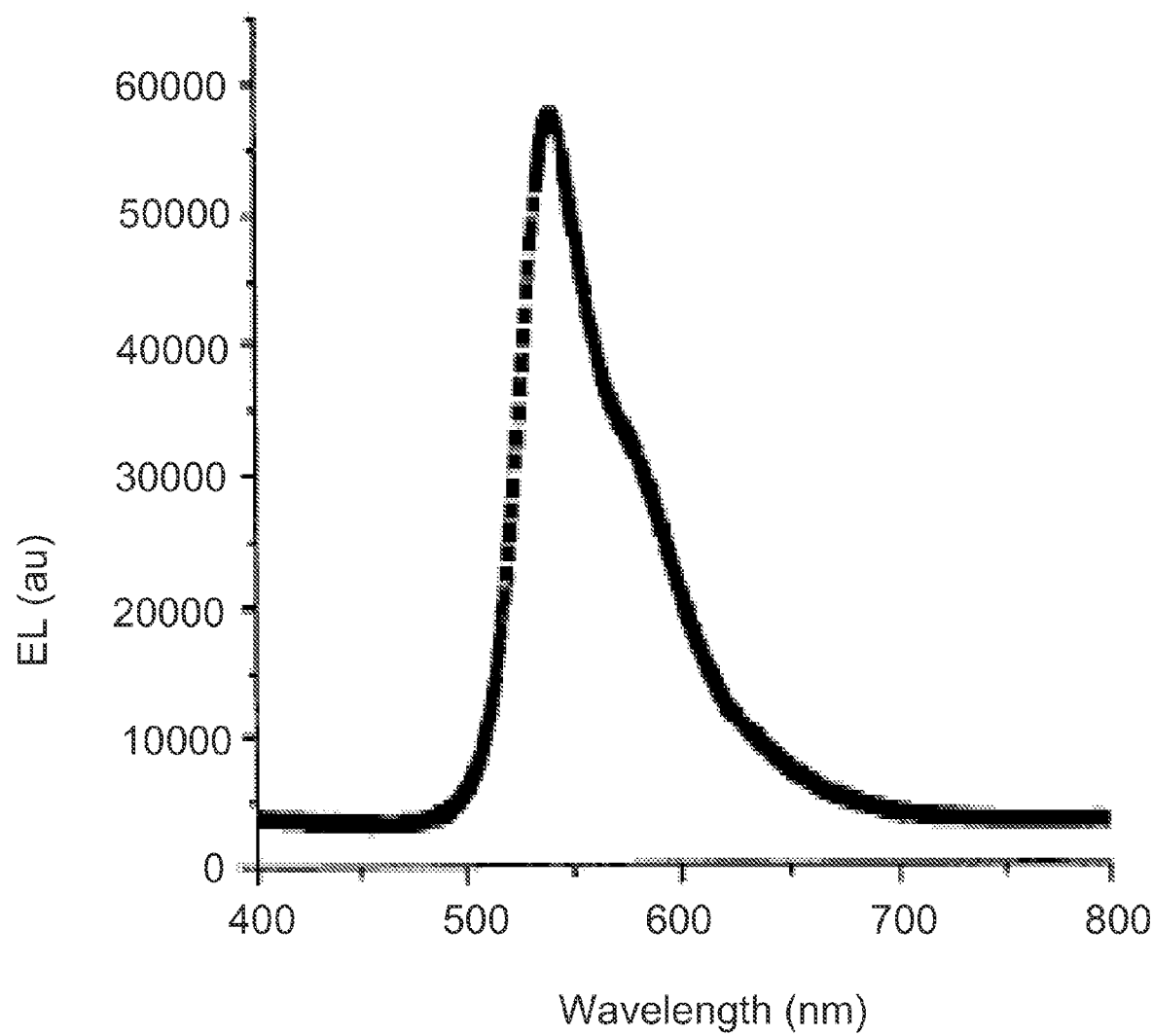
FIG. 7 shows the electroluminescence spectrum of dendrimer A-8.
Figure 8:
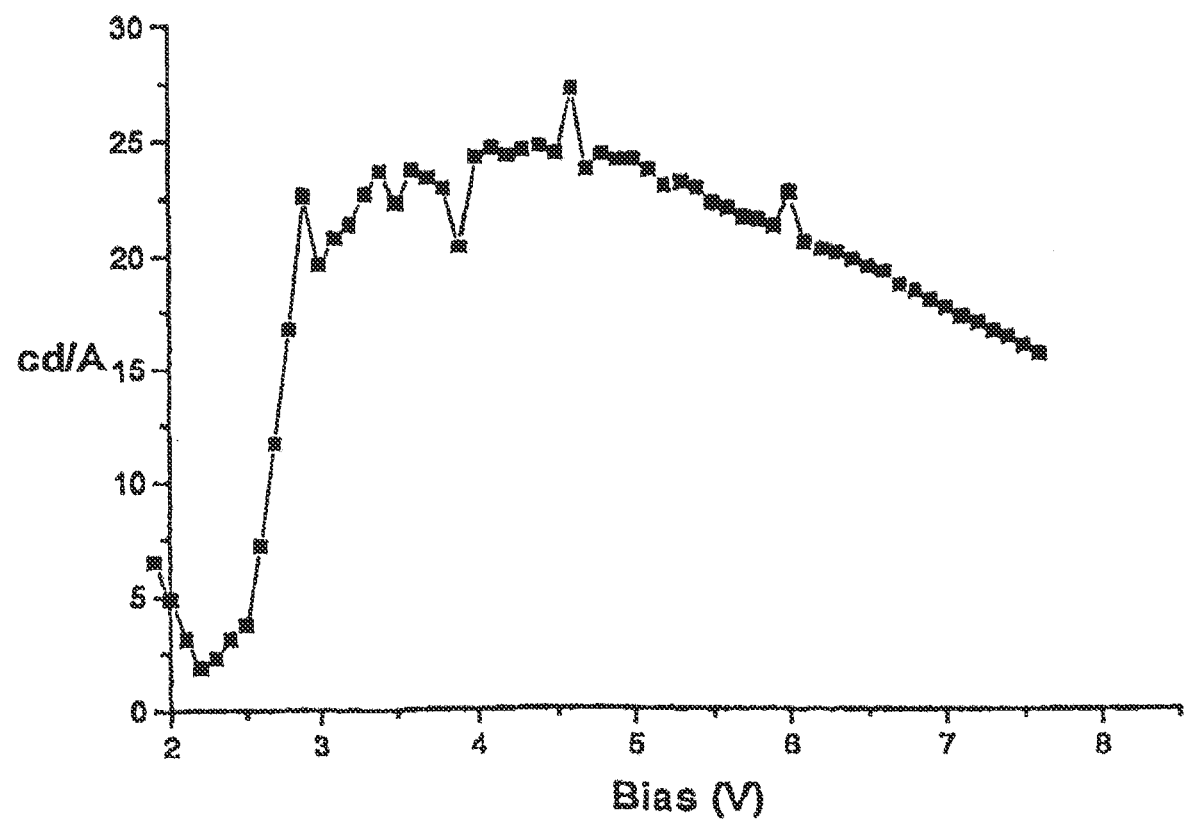
FIG. 8 shows the external efficiency of an OLED device containing dendrimer A-8.
Figure 9:
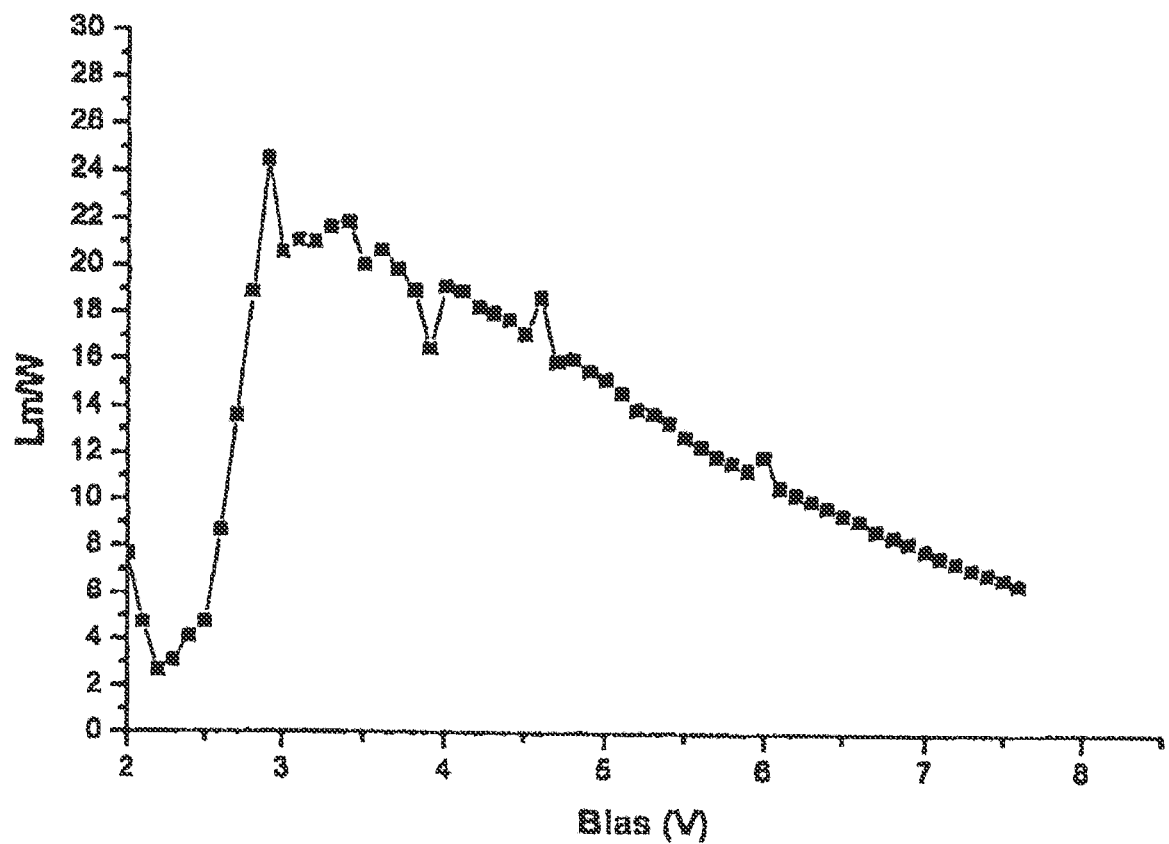
FIG. 9 shows the luminous efficiency of an OLED device containing dendrimer A-8.
Figure 10:
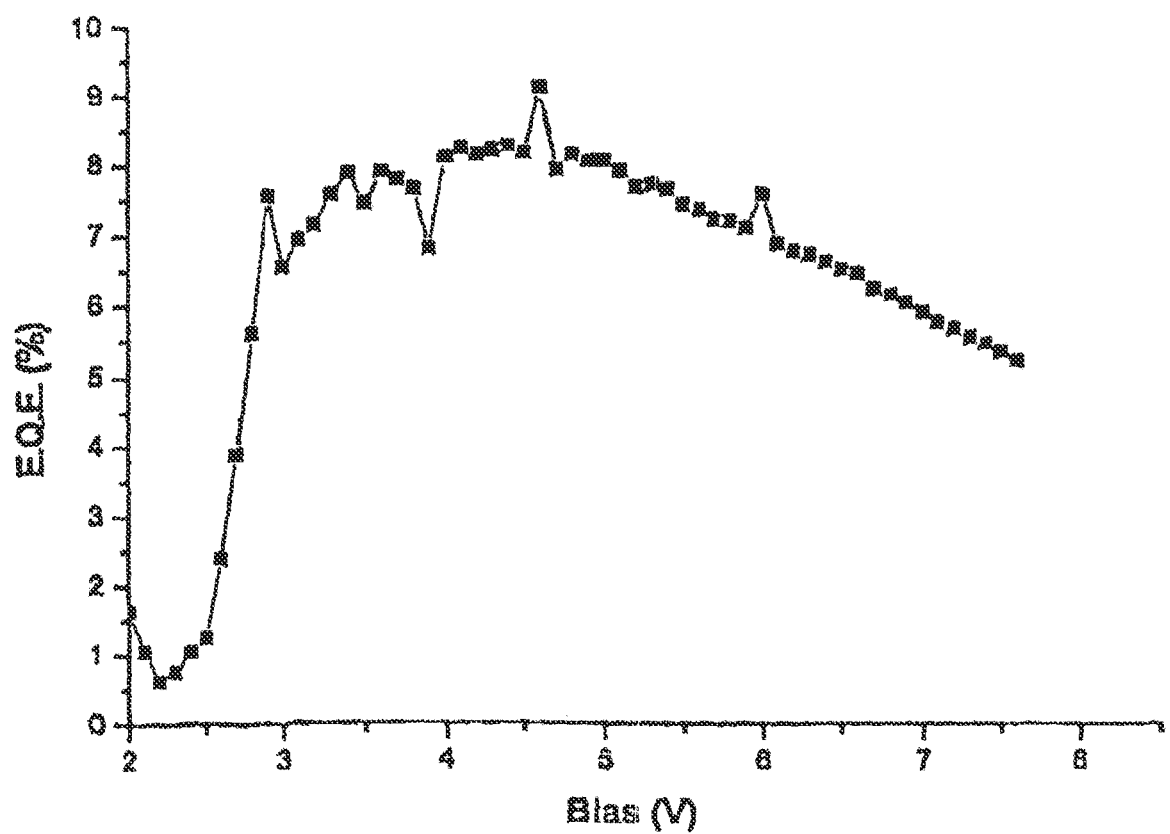
FIG. 10 shows the external quantum efficiency of an OLED device containing dendrimer A-8.
Figure 11:
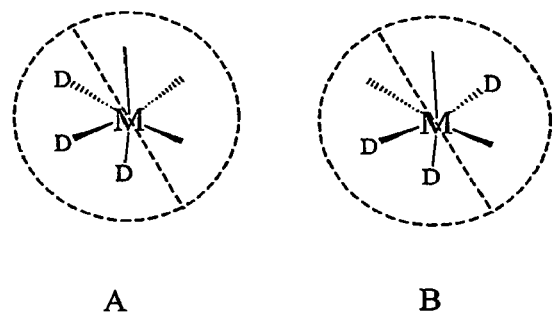
FIG. 11 shows diagrammatically the requirements for the dendrimers of the present invention.
Figure 11:
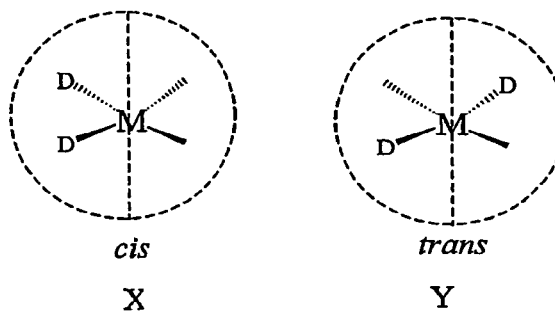

A two layer device was prepared with A-8 by the following method. The ITO on glass was cleaned using an Emitech plasma Asher. O$_2$ flow rate was set to 10, RF power to 70 watts and duration of cleaning was 4 min. Substrates were then loaded into a spin-coater straight away and A-8 in chloroform at a concentration of 10 mg/ml was spin-coated at 2000 rpm for 60 sec. The device was completed by sequential evaporation of TPBI, LiF, and Al to give a device structure of: ITO/A-8/TPBI(50 nm)/LiF(0.9 nm)/Al(60 nm). The device properties are shown in FIGS. 7 to 10; the maximum efficiency was 22 lm/W at 3.5V. The C/E coordinates are x=0.5, y=0.5. These results should be compared to the first generation dendrimer (IrppyD1) with only one dendron attached to each ligand. In a device configuration of ITO/IrppyD1/BCP/LiF/Al the maximum efficiency was 0.14 lm/W (0.47 cd/A) at 9.5 V (S.-C. Lo, et al *Adv. Mater.*, 2002, 13, 975). Although the electron transport/hole blocking layers are different they would not be expected to give over two orders of magnitude difference in this case. This further illustrates the surprising improvements given by the present invention.

A two layer device was prepared with B-4 that had the structure ITO/B-4/TPBI/LiF 90.8 nm)/Al (100 nm) It was fabricated using the same procedures used for the device containing A-8, although the dendrimer was spin-coated from a 20 mg/ml solution at 2000 rpm. The maximum efficiency of this device was 38 lm/W. At 100 cd/m$^2$ and 4.8 V the EQE was 13.2%, 45 cd/A and power efficiency was 30 lm/W. The CM coordinates of the emission are x=0.47, and y=0.52 which is slightly blue shifted relative to A-8 due to the different attachment position of the dendron on the pyridine ring. The efficiency of the device containing B-4 is even higher than the efficiency of the device containing A-8. It should be noted that both dendrimers can be used as a single component in the light emitting layer and do not need to be blended with a host material to give high efficiency devices which further illustrates the advantages of the current invention.

The invention claimed is:

1. A charge-neutral organometallic dendrimer of formula (II):

M-[X(DENDRITE(-Q)$_a$)$_y$]$_x$Y$_z$ (II)

in which M represents a metal cation, x represents an integer of 2 or more, y represents an integer of 2 or more, each X which may be the same or different represents a bi-dentate coordinating group, z represents 0 or an integer of 1 or more, and each Y which may be the same or different represents a coordinating group, the total of (2.x)+(c.z) being equal to the number of coordination sites on M, wherein c is the number of coordination sites on Y; each DENDRITE which may be the same or different represents a dendritic molecular structure bonded to a group X, wherein each X terminates in the first single bond which is connected to a branching group or branching atom of DENDRITE; a represents 0 or an integer of 1 or more; and each Q which may be the same or different represents a surface group;

wherein:
the metal cation is iridium or platinum;
x represents an integer of 2 or 3;
each X, which may be the same or different, represents a bidentate coordinating group of the following formula:

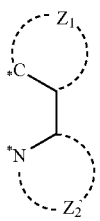

wherein * represents a bond to M and $Z_1$ and $Z_2$ are groups required to complete 5 or 6 membered aryl or heteroaryl rings, wherein:
$Z_1$ is such that the 5 or 6 membered aryl or heteroaryl ring, which can optionally be part of a fused ring system, is selected from phenyl, pyridyl, thiophenyl, naphthyl, anthryl, phenanthryl, benzamidazolyl, carbazolyl, fluorenyl, pyrimidinyl pyrazinyl, pyridazinyl, quinolinyl, isoquinolinyl, quinoxalinyl, benzothiophenyl, phthalazinyl, quinazolinyl, imidazolyl, pyrazolinyl, oxazolinyl, oxadiazolinyl, triazolyl, triazinyl, thiadiazolyl, benzimidazolyl, benzoxazolyl, phenanthridinyl, furyl and benzothiophenyl; and
$Z_2$ is such that the 5 or 6 membered aryl or heteroaryl ring which can optionally be part of a fused ring system is selected from pyridine, pyrimidine, pyrazine, pyridazine, quinoline, isoquinoline, quinoxaline, phthalazine, quinazoline, naphtholidine, cinnoline, pyrimidine, phenanthroline, imidazole, pyrazole, oxazole, oxadiazole, triazole, thiadiazole, benzimidazole, benzoxazole, benzthiazole and phenanthridine;
each Y, which may be the same or different, represents a coordinating group selected from: a ligand of formula (IV)

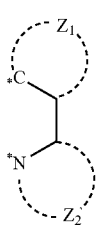

in which $Z_1$ and $Z_2$ are as defined above and each * represents a bond to M; a β-diketonate; a 2-carboxylpyridine; a triarylphosphine; a trialkylphosphine; ethylenediamine; cyanide; carbon monoxide and carbon monosulfide;
each DENDRITE, which may be the same or different, represents an at least partially conjugated dendritic molecular structure bonded to a group X, which dendritic molecular structure comprises aryl and/or heteroaryl groups or nitrogen and, optionally, vinyl or acetylenyl groups, connected via $sp^2$ hybridised carbon atoms of said (hetero)aryl or vinyl groups, or via sp hybridised carbon atoms of said acetylenyl groups, or via single bonds between N and (hetero)aryl groups, each X terminating in the first single bond which is connected to either: (a) an $sp^2$ hybridised (ring) carbon atom of the first (hetero)aryl group to which more than one at least partially conjugated dendritic branch is attached, or (b) a nitrogen atom to which more than one at least partially conjugated dendritic branch is attached, said ring carbon atom or N forming part of said DENDRITE; and
each Q which may be the same or different represents a surface group selected from a further-reactable alkene; a (meth)acrylate group; a sulphur-containing group, a silicon-containing group; a sulphonyl group; a polyether group; a $C_1$-to-$C_{15}$ alkyl group; an amine group; a mono-, di- or tri-$C_1$-to-$C_{15}$ alkyl amine group; a —COOR group wherein R is hydrogen or $C_1$-to-$C_{15}$ alkyl; an —OR group wherein R is hydrogen, aryl, or $C_1$-to-$C_{15}$ alkyl or alkenyl; an —$O_2$SR group wherein R is $C_1$-to-$C_{15}$ alkyl or alkenyl; an —SR group wherein R is aryl, or $C_1$-to-$C_{15}$ alkyl or alkenyl; and an —$SiR_3$ group wherein the R groups are the same or different and are hydrogen, $C_1$-to-$C_{15}$ alkyl or alkenyl, or —SRN group (RN is aryl or $C_1$-to-$C_{15}$ alkyl or alkenyl), aryl, or heteroaryl.

2. An organometallic dendrimer according to claim 1 which is formula (III):

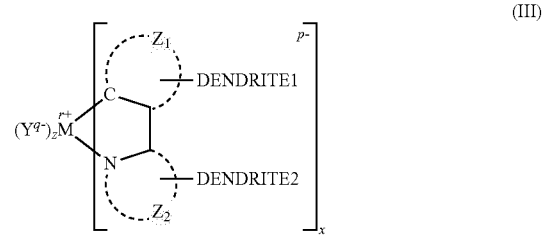

in which M is a metal cation with formal charge r+, $Z_1$ and $Z_2$ are groups required to complete 5 or 6-membered aryl or heteroaryl rings which can be optionally substituted, DENDRITE1 and DENDRITE2 are dendritic molecular structures, Y is a neutral or anionic ligand, and each Y can be the same or different if z is greater than 1;
wherein:
the metal cation is iridium or platinum;
x represents an integer of 2 or 3;

$Z_1$ is such that the 5 or 6 membered aryl or heteroaryl ring, which can optionally be part of a fused ring system, is selected from phenyl, pyridyl, thiophenyl, naphthyl, anthryl, phenanthryl, benzamidazolyl, carbazolyl, fluorenyl, pyrimidinyl, pyrazinyl, pyridazinyl, quinolinyl, isoquinolinyl, quinoxalinyl, benzothiophenyl, phthalazinyl, quinazolinyl, imidazolyl, pyrazolinyl, oxazolinyl, oxadiazolinyl, triazolyl, triazinyl, thiadiazolyl, benzimidazolyl, benzoxazolyl, phenanthridinyl, furyl and benzothiophenyl;

$Z_2$ is such that the 5 or 6 membered aryl or heteroaryl ring which can optionally be part of a fused rinq system is selected from pyridine, pyrimidine, pyrazine, pyridazine, quinoline, isoquinoline, quinoxaline, phthalazine, quinazoline, naphtholidine, cinnoline, pyrimidine, phenanthroline, imidazole, pyrazole, oxazole, oxadiazole, triazole, thiadiazole, benzimidazole, benzoxazole, benzthiazole and phenanthridine;

each Y, which may be the same or different, represents a coordinating group selected from: a ligand of formula (IV)

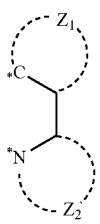

(IV)

in which $Z_1$ and $Z_2$ are as defined above and each * represents a bond to M; a β-diketonate; a 2-carboxylpyridine; a triarylphosphine; a trialkylphosphine; ethylenediamine; cyanide; carbon monoxide and carbon monosulfide;

DENDRITE1 represents an at least partially conjugated dendritic molecular structure, which dendritic molecular structure comprises aryl and/or heteroaryl groups or nitrogen and, optionally, vinyl or acetylenyl groups, connected via $sp^2$ hybridised carbon atoms of said (hetero)aryl or vinyl groups, or via sp hybridised carbon atoms of said acetylenyl groups, or via single bonds between N and (hetero)aryl groups, the group $Z_1$ to which DENDRITE1 is bonded terminating in the first single bond which is connected to either: (a) an $sp^2$ hybridised (ring) carbon atom of the first (hetero)aryl group to which more than one at least partially conjugated dendritic branch is attached, or (b) a nitrogen atom to which more than one at least partially conjugated dendritic branch is attached, said ring carbon atom or nitrogen atom forming part of DENDRITE1; and DENDRITE2 represents an at least partially conjugated dendritic molecular structure, which dendritic molecular structure comprises aryl and/or heteroaryl groups or nitrogen and, optionally, vinyl or acetylenyl groups, connected via $sp^2$ hybridised carbon atoms of said (hetero)aryl or vinyl groups, or via sp hybridised carbon atoms of said acetylenyl groups, or via single bonds between N and (hetero)aryl groups, the group $Z_2$ to which DENDRITE2 is bonded terminating in the first single bond which is connected to either: (a) an $sp^2$ hybridised (ring) carbon atom of the first (hetero)aryl group to which more than one at least partially conjugated dendritic branch is attached, or (b) a nitrogen atom to which more than one at least partially conjugated dendritic branch is attached, said ring carbon atom or nitrogen atom forming part of DENDRITE2.

3. An organometallic dendrimer according to claim 1 wherein x is 3 and z is 0.

4. An organometallic dendrimer according to claim 1 wherein the metal cation is iridium.

5. An organometallic dendrimer according to claim 1 wherein the metal cation is platinum.

6. A film consisting essentially of an organometallic dendrimer according to claim 1.

7. A film comprising an organometallic dendrimer according to claim 1 and one or more molecular, dendritic or polymeric compounds.

8. A film according to claim 7 wherein the molar ratio of the organometallic dendrimer to the one or more molecular, dendritic, or polymeric compounds is from 1:1 to 100:1.

9. An organic light-emitting device comprising, in sequence, layers of an optional substrate, an electrode, a first optional charge-transporting layer, a light-emissive layer, a second optional charge-transporting layer and a counter electrode, wherein at least one of the light-emissive layer, first optional charge-transporting layer and second optional charge-transporting layers is a film comprising an organometallic dendrimer according to claim 1.

10. An organic light-emitting device comprising, in sequence, layers of an optional substrate, an electrode, a first optional charge-transporting layer, a light-emissive layer, a second optional charge-transporting layer and a counter electrode, wherein the light-emissive layer is a film comprising an organometallic dendrimer according to claim 1.

11. A device according to claim 9 which comprises at least one charge-transporting layer.

12. A device according to claim 9 wherein the light-emissive layer comprises an emissive dopant, as additional component.

13. A device according to claim 9 wherein the light-emissive layer comprises one or more charge-transporting species, as additional component.

14. A device according to claim 9 wherein the light-emissive layer comprises a molecular or dendritic species, as additional component.

15. A device according to claim 9 wherein the light-emissive layer comprises a polymer, as additional component.

16. A device according to claim 12 wherein the additional component represents 95 to 5 mol % of the total composition.

17. A device according to claim 9 that is an organic light-emitting diode (OLED).

18. A photovoltaic device that comprises at least a layer of a film comprising an organometallic dendrimer according to claim 1.

19. A charge-neutral organometallic dendrimer of formula (B-4):

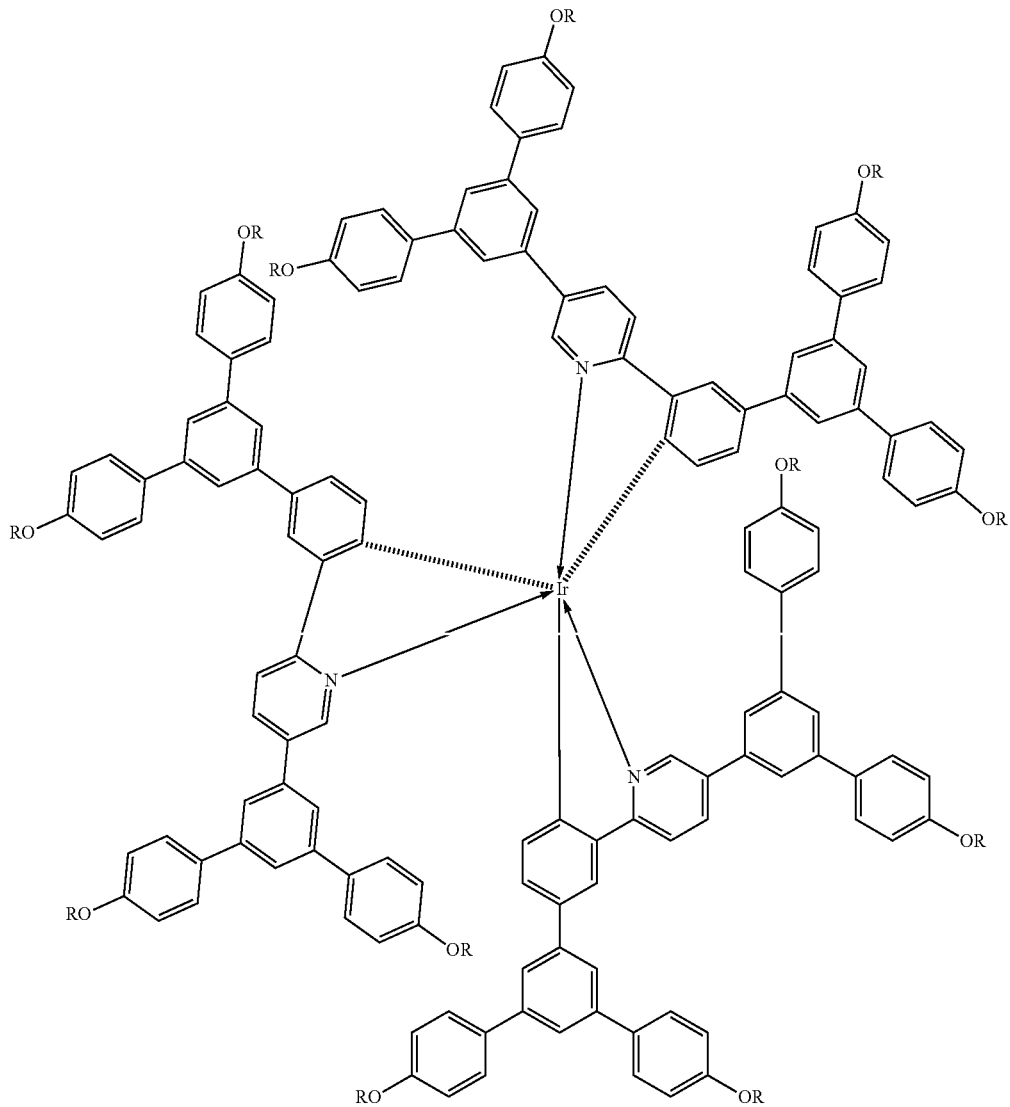

(B-4)

wherein R is hydrogen, aryl, or $C_1$-to-$C_{15}$ alkyl or alkenyl.

20. A charge-neutral organometallic dendrimer according to claim 19 wherein R is 2-ethylhexyl.

21. A film consisting essentially of an organometallic dendrimer according to claim 19.

22. A film comprising an organometallic dendrimer according to claim 19 and one or more molecular, dendritic or polymeric compounds.

23. A film according to claim 22 wherein the molar ratio of the organometallic dendrimer to the one or more molecular, dendritic or polymeric compounds is from 1:1 to 100:1.

24. An organic light-emitting device comprising, in sequence, layers of an optional substrate, an electrode, a first optional charge-transporting layer, a light-emissive layer, a second optional charge-transporting layer and a counter electrode, wherein at least one of the light-emissive layer, first optional charge-transporting layer and second optional charge-transporting layers is a film comprising an organometallic dendrimer according to claim 19 or a film according to claim 22.

25. An organic light-emitting device comprising, in sequence, layers of an optional substrate, an electrode, a first optional charge-transporting layer, a light-emissive layer, a second optional charge-transporting layer and a counter electrode, wherein the light-emissive layer is a film comprising an organometallic dendrimer according to claim 19 or a film according to claim 22.

26. A device according to claim 24 wherein the light-emissive layer comprises an emissive dopant, as additional component.

27. A device according to claim 24 wherein the light-emissive layer comprises one or more charge-transporting species, as additional component.

28. A device according to claim 24 wherein the light-emissive layer comprises a molecular or dendritic species, as additional component.

29. A device according to claim 24 wherein the light-emissive layer comprises a polymer, as additional component.

* * * * *

UNITED STATES PATENT AND TRADEMARK OFFICE
CERTIFICATE OF CORRECTION

PATENT NO. : 8,536,333 B2
APPLICATION NO. : 12/854288
DATED : September 17, 2013
INVENTOR(S) : Samuel et al.

It is certified that error appears in the above-identified patent and that said Letters Patent is hereby corrected as shown below:

In the Claims

Claim 2, at column 19, line 12 by replacing [rinq] with ring.

Signed and Sealed this
Fifteenth Day of October, 2013

Teresa Stanek Rea
*Deputy Director of the United States Patent and Trademark Office*